(12) United States Patent
Zhu et al.

(10) Patent No.: US 10,494,489 B2
(45) Date of Patent: *Dec. 3, 2019

(54) LOW TEMPERATURE AND EFFICIENT FRACTIONATION OF LIGNOCELLULOSIC BIOMASS USING RECYCLABLE ORGANIC SOLID ACIDS

(71) Applicant: The United States of America as Represented by the Secretary of Agriculture, Washington, DC (US)

(72) Inventors: Junyong Zhu, Madison, WI (US); Liheng Chen, Madison, WI (US); Roland Gleisner, Jefferson, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 16/356,327

(22) Filed: Mar. 18, 2019

(65) Prior Publication Data

US 2019/0233596 A1   Aug. 1, 2019

Related U.S. Application Data

(63) Continuation-in-part of application No. 15/882,078, filed on Jan. 29, 2018, now Pat. No. 10,239,905.

(60) Provisional application No. 62/452,282, filed on Jan. 30, 2017.

(51) Int. Cl.
| | | |
|---|---|---|
| *C12P 19/14* | (2006.01) | |
| *C08H 8/00* | (2010.01) | |
| *D21C 3/00* | (2006.01) | |
| *C07D 307/36* | (2006.01) | |
| *C12P 19/00* | (2006.01) | |

(52) U.S. Cl.
CPC ............. *C08H 8/00* (2013.01); *C07D 307/36* (2013.01); *C12P 19/00* (2013.01); *D21C 3/003* (2013.01)

(58) Field of Classification Search
CPC combination set(s) only.
See application file for complete search history.

(56) References Cited

U.S. PATENT DOCUMENTS 10,239,905 B2 * 3/2019 Zhu .......................... C07G 1/00

* cited by examiner

*Primary Examiner* — Tekchand Saidha

(57) ABSTRACT

Methods of fractionating lignocellulosic biomass using hydrotropic solid organic acids are provided. Also provided are methods of forming lignin particles, furans, sugars, and/or lignocellulosic micro- and nanofibrils from the liquid and solid fractions produced by fractionation process. The fractionation can be carried out at low temperatures with short reaction times.

14 Claims, 39 Drawing Sheets

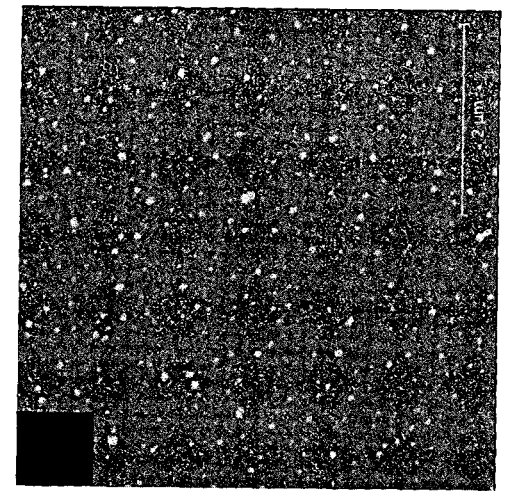
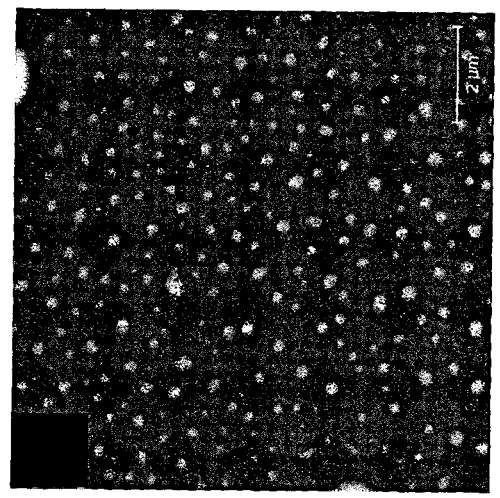
FIG. 16C
FIG. 16B
FIG. 16A 240 times/min

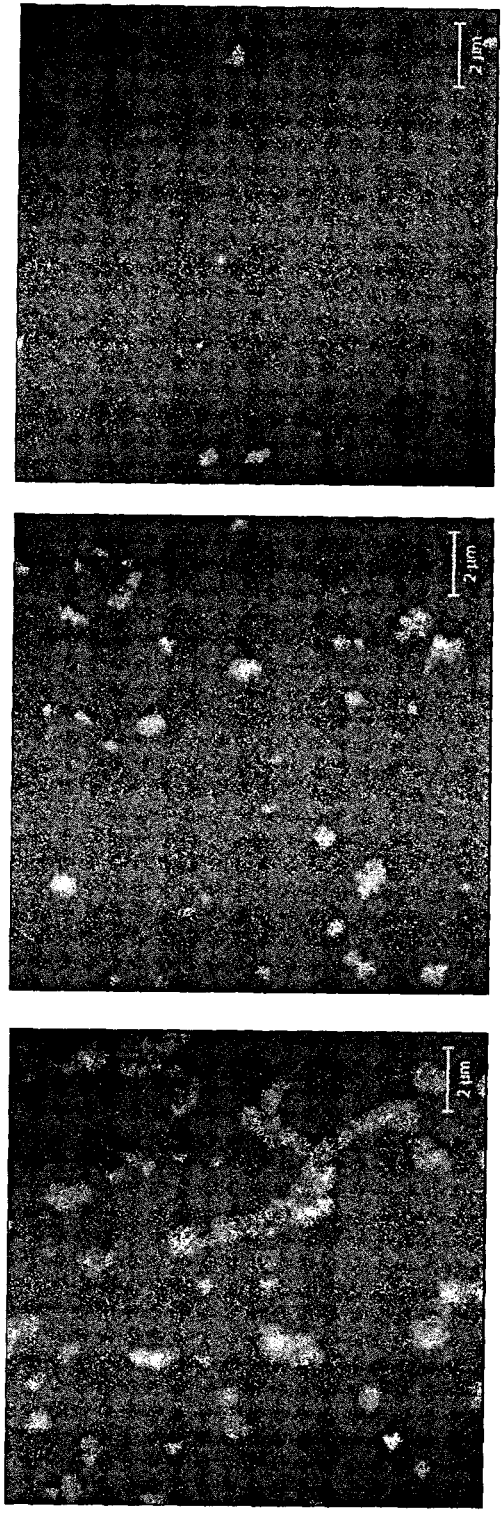

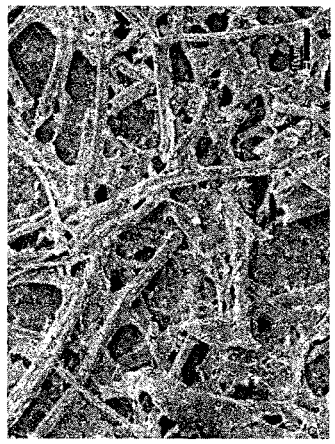
FIG. 33A
FIG. 33B
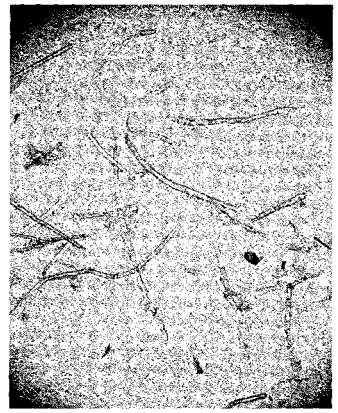
Scanning Electronic Microscopy (SEM)
Optical Microscopy
Delignified and refined CSF = 650 mL
Delignified and refined CSF = 450 mL

FIG. 38A

| Sample Label | Material insoluble Solids (MIS) | | | | | Yeast liquor | | | | |
|---|---|---|---|---|---|---|---|---|---|---|
| | Solids yield (%) | Glucan (%) | Xylan (%) | Mannan (%) | Lignin (%) | Glucose (g/L) | Xylose (g/L) | Mannose (g/L) | Acetic acid (g/L) | Furfural[2] (g/L) |
| Untreated M222 | 100 | 45.7 | 14.9 | 4.6 | 23.4 | | | | | |
| P30T10t30 | 95.5 | 43.9 (91.6) | 13.8 (88.5) | 1.8 (37.1) | 23.3 (95.0) | | | | | |
| P30T10t30 | 96.0 | 44.3 (92.7) | 13.6 (87.7) | 2.8 (58.1) | 22.7 (93.0) | | | | | |
| P30T50t60 | 89.2 | 45.0 (87.7) | 13.3 (79.7) | 2.1 (40.5) | 22.7 (86.4) | | | | | |
| P40T50t30 | 89.3 | 42.9 (83.7) | 13.1 (78.6) | 2.1 (40.5) | 23.9 (91.1) | | | | | |
| P20T10t60 | 82.8 | 48.7 (88.1) | 15.1 (84.0) | 2.1 (37.6) | 23.7 (83.7) | | | | | |
| P30T30t30 | 94.7 | 44.3 (91.7) | 13.9 (88.4) | 2.2 (45.0) | 22.9 (92.5) | | | | | |
| P70T50t09 | 77.2 | 59.2 (100) | 8.8 (45.4) | 4.0 (67.4) | 20.9 (68.8) | | | | | |
| P70T50t20 | 78.9 | 56.8 (97.9) | 8.8 (46.7) | 3.3 (56.4) | 20.6 (69.4) | | | | | |
| P70T65t20 | 68.4 | 61.6 (92.2) | 6.5 (29.8) | 4.3 (63.9) | 11.8 (34.4) | | | | | |
| P70T50t35 | 74.4 | 62.2 (101.1) | 7.4 (37.0) | 4.3 (68.9) | 19.2 (61.0) | 1.1 (2.2) | 8.9 (52.4) | 1.0 (20.3) | 1.1 | 0.05 (0.5) |
| P70T65t35 | 64.1 | 68.0 (95.3) | 6.6 (28.4) | 4.6 (64.0) | 13.0 (35.7) | 1.3 (2.5) | 10.1 (59.5) | 1.5 (29.9) | 1.5 | 0.08 (0.7) |
| P70T80t35 | 55.5 | 67.3 (81.7) | 4.9 (18.3) | 4.2 (50.5) | 6.7 (15.8) | 1.8 (3.6) | 11.6 (68.3) | 2.0 (38.7) | 1.5 | 0.19 (1.7) |
| P70T80t20 | 58.9 | 63.0 (81.1) | 6.5 (24.5) | 4.3 (53.8) | 8.8 (22.1) | 1.5 (3.0) | 11.0 (65.0) | 1.8 (35.2) | 1.6 | 0.13 (1.2) |
| P75T65t05 | 67.1 | 56.2 (82.4) | 6.5 (29.3) | 4.1 (60.0) | 15.0 (42.9) | 1.2 (2.4) | 10.1 (59.7) | 1.5 (29.3) | 1.5 | 0.07 (0.6) |

FIG. 38B

| Sample | Solids yield (%) | Glucan (%) | Xylan (%) | Mannan (%) | Lignin (%) | Glucose (g/L) | Xylose (g/L) | Mannose (g/L) | Acetic acid (g/L) | Furfural [2] (g/L) |
|---|---|---|---|---|---|---|---|---|---|---|
| P75T60/40 | 60.7 | 71.8 (95.4) | 5.8 (23.8) | 4.9 (63.7) | 10.8 (28.0) | 1.4 (2.7) | 10.8 (64.0) | 1.7 (32.4) | 1.5 | 0.10 (0.9) |
| P75T65/35 | 59.0 | 71.7 (94.5) | 6.0 (23.9) | 4.0 (51.3) | 8.9 (22.3) | 1.3 (2.6) | 10.3 (60.8) | 1.7 (32.4) | 1.4 | 0.10 (0.9) |
| P75T65/60 | 57.0 | 74.7 (93.1) | 5.0 (19.2) | 4.3 (52.8) | 7.4 (17.9) | 1.7 (3.2) | 10.7 (63.4) | 1.8 (34.6) | 1.5 | 0.14 (1.2) |
| P75T60/70 | 55.0 | 72.4 (87.1) | 5.2 (19.1) | 4.4 (52.7) | 6.1 (14.4) | 1.8 (3.6) | 10.9 (64.2) | 2.0 (39.7) | 1.5 | 0.19 (1.7) |
| P80T80/20 | 51.9 | 72.3 (81.9) | 3.7 (13.0) | 3.7 (41.8) | 4.2 (9.2) | 2.3 (4.6) | 9.9 (58.4) | 2.2 (43.9) | 1.4 | 0.33 (3.1) |
| P80T80/15 | 50.8 | 75.0 (83.4) | 3.6 (12.3) | 2.9 (31.7) | 4.8 (10.4) | | | | | |
| P80T80/60 | 57.6 | 68.2 (85.9) | 3.2 (12.4) | 2.4 (30.0) | 8.3 (20.3) | | | | | |
| P85T50/15 | 49.2 | 75.0 (80.6) | 5.0 (16.5) | 3.5 (37.2) | 5.8 (12.2) | | | | | |
| P85T60/20 | 49.6 | 72.3 (78.4) | 4.8 (16.0) | 3.4 (36.4) | 3.3 (7.0) | | | | | |
| P80T80/30 | 55.9 | 68.9 (86.0) | 5.0 (18.8) | 3.6 (43.5) | 8.7 (20.8) | | | | | |
| P80T60/90 | 51.8 | 70.7 (80.1) | 2.6 (9.0) | 2.7 (30.4) | 15.1 (33.4) | | | | | |
| P80T70/10 | 55.4 | 79.1 (95.8) | 2.1 (8.8) | 2.0 (24.6) | 3.5 (8.3) | | | | | |
| P80T70/20 | 47.2 | 80.2 (82.8) | 2.2 (9.8) | 2.2 (22.6) | 4.4 (8.8) | | | | | |

LOW TEMPERATURE AND EFFICIENT FRACTIONATION OF LIGNOCELLULOSIC BIOMASS USING RECYCLABLE ORGANIC SOLID ACIDS

CROSS-REFERENCE TO RELATED APPLICATIONS

The present application is a continuation of U.S. patent application Ser. No. 15/882,078 that was filed on Jan. 29, 2018, which claims priority to U.S. provisional patent application No. 62/452,282 that was filed on Jan. 30, 2017, the entire contents of both of which are hereby incorporated herein by reference.

FIELD OF THE INVENTIONS

The inventions described herein relate to the field of fractionation of lignocellulosic plant biomass, such as wood biomass, for value added utilizations.

BACKGROUND

The per capita demand for cellulosic fibers in textiles is expected to increase from 3.7 to 5.4 kg in the next 15 years. With the Earth's population estimated to grow from 6.9 to 8.3 billion in the same time period, it is expected that cotton, a major source of cellulosic fibers, will not meet market demand due to the estimated production of only 3.1 kg per capita in 2030, based on anticipated shrinkage of cotton growing area (Hauru et al. 2013). Therefore, producing man-made cellulosic-based fibers, such as viscose, cellulose acetate, etc., from dissolving pulp will be a necessary alternative to make up this large market shortage of at least 1.7 kg per capita for native cellulosic fibers. Dissolving pulp fibers are commercially produced using either sulfite pulping or hot-water pre-hydrolysis coupled with kraft pulping, both developed in the 1950's. The main problems with sulfite pulping are chemical recovery and environmental concerns due to $SO_2$ air emissions. The metal base in sulfite pulping, excepting magnesium, cannot be recovered. Pre-hydrolysis with kraft pulping is very expensive in terms of energy. Chemical recovery in kraft pulping is commercially practiced using the Tomlinson recovery boiler, but is capital intensive. The hemicellulosic sugars from hot-water pre-hydrolysis are often discarded to save energy, which can create substantial biochemical oxygen demand (BOD) problems.

Cellulose nanomaterials have attracted great attention recently for their unique optical and mechanical properties (Moon et al. 2011; Zhu et al. 2016). Most of the published research, however, has been focused on cellulose nanomaterials produced using bleached fibers that do not contain lignin. Lignin is relatively hydrophobic, which can be beneficial for certain applications. Unfortunately, only a few studies have reported the production of lignin containing cellulose nanomaterials from commercial unbleached chemical pulps using direct mechanical fibrillation, which is energy intensive and does not produce surface functional groups which aid dispersion (Rojo et al. 2015; Spence et al. 2010). A study on the production of lignocellulose nanomaterials directly from wood is reported as a patented process by American Process, Inc. at high temperatures using an organic solvent solution of concentrated ethanol and sulfur dioxide (Nelson et al. 2015).

Nano sized particles have attracted great interest due to their large specific surface areas and shape dependent properties for a variety of potential applications (Xia et al. 2009). Organic nanoparticles (Kamaly et al. 2016; Mavila et al. 2016; Reisch and Klymchenko 2016), especially those derived from biodegradable and benign natural biopolymers, such as cellulose, chitin and DNA, are more attractive from a sustainability point of view. Lignin, the second most abundant natural polymer from a plant biomass cell wall, has so far found limited economical utilization other than as a boiler fuel through combustion in pulp mills (Duval and Lawoko 2014; Upton and Kasko 2016). With rapid advances in nanotechnology, lignin, as a renewable and abundant biopolymer, has gained growing interests in the nanotechnology field (Frangville et al. 2012; Nair et al. 2014). Lignin nanoparticles (LNPs) have potential applications in developing novel and biodegradable materials and advancing biotechnologies (Jiang et al. 2013; Qian et al. 2014; Richter et al. 2015; Ten et al. 2014).

The commercial applications of LNPs through industrial processing, however, are impeded by the difficulties in economical production from the plant cell wall. Almost all of the existing methods for the production of LNPs use commercial technical lignin which requires dissolution in solvents, such as ethylene glycol, acetone, tetrahydrofuran (THF), or N,N-dimethylformamide (DMF), followed by either acidic precipitation (Frangville et al. 2012; Richter et al. 2016), hexane precipitation (Qian et al. 2014), dialysis (Lievonen et al. 2016), or atomization and drying (Ago et al. 2016). The use of organic solvents such as ethylene glycol and THF is an environmental concern and increases LNP cost for solvent recovery. Also, the LNP properties are affected by the original feed lignin sources generated from various pulping processes.

Hydrotropic chemistry using concentrated aromatic salts as solvents for solubilizing a range of hydrophobic compounds was discovered in 1916 by Neuberg. Its application for fractionation of lignocellulosic biomass was first practiced by McKee (McKee 1943). For pulping poplar using 30-40 weight percent (wt %) aqueous sodium xylenesulfonate liquor, a reaction of temperature of 150° C. for 11-12 hr was needed to obtain a cellulosic solids yield of 52% (McKee 1946). There are many hydrotropic agents that can be used to dissolve lignin (Procter 1971). The most used salts were sodium salicylate and xylenesulfonate, cumenesulfonate. Sodium xylenesulfonate was found to have very strong hydrotropic activity at 30 wt % and only required a 3-time dilution to lose its hydrotropic properties and, thus, precipitate lignin (Robert 1955). There have been numerous studies on hydrotropic pulping since its invention (Gromov and Odincov 1959; McKee 1954; Procter 1971) including using additives (Kalninsh et al. 1967; Nelson 1978). However, the processes were never commercialized due to low pulp yields, poor pulp mechanical properties, and very long cooking times. Moreover, the processes were not suitable for pulping softwoods, due to insufficient delignification (Procter 1971). Recently, hydrotropic pulp was found to be enzymatically digestible for sugar production (Korpinen and Fardim 2009). To reduce reaction time, additives such as formic acid and hydrogen peroxide were used (Gabov et al. 2013). A recent study included the characterization of lignin from modified hydrotropic processes used for subsequent sugar production (Gabov et al. 2014). The utilization of hydrotropic lignin, however, has remained limited (Kalninsh et al. 1962; Procter 1971).

SUMMARY

Methods of treating lignocellulosic biomass to fractionate the lignocellulosic biomass and/or to dissolve lignin are provided.

One embodiment of a method for treating lignocellulosic biomass includes dispersing a lignocellulosic biomass in an aqueous solution comprising a sulfonic acid, such as p-toluenesulfonic acid. The concentration of the sulfonic acid in the solution is higher than its minimal hydrotrope concentration so that lignin in the lignocellulosic biomass is dissolved. The solution is maintained at a temperature and for a time sufficient to dissolve at least 10 wt. % of the lignin in the lignocellulosic biomass. The solution and the dispersed lignocellulosic biomass can then be separated into a spent acid solution comprising dissolved lignin and a water-insoluble cellulose-rich solids fraction referred to as water-insoluble lignocellulosic solid residues (LCSR).

Optionally, the spent acid solution and/or the water-insoluble lignocellulosic solid residues can then the further processed. For example, the spent acid solution can be further processed by precipitating out lignin nanoparticles and/or by converting dissolved sugars into furans, which can be separated from the spent acid solution. The lignocellulosic solid residues can be further processed into lignocellulosic microfibrils, lignocellulosic nanofibrils, or a combination thereof via mechanical fibrillation and/or by converting them into sugars via hydrolysis.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 16A is an AFM image of lignin particle aggregates in a supernatant centrifuged at a centrifuge speed of 3000 g with a lateral size of approximately 600 nm, as described in Example 11. FIG. 16B is an AFM image of small lignin particle aggregates in a supernatant centrifuged at a centrifuge speed of 10000 g. FIG. 16C is an AFM image of lignin particle aggregates in a supernatant centrifuged at a centrifuge speed of 15000 g

FIG. 24A is an AFM image of the LNPs of Example 12 for an NaCl concentration of 10 mM. FIG. 24B is an AFM image of the LNPs of Example 12 for an NaCl concentration of 33 mM. FIG. 24C is an AFM image of the LNPs of Example 12 for an NaCl concentration of 5 mM.

FIG. 33A shows and optical micrograph (left panel) and an SEM image (right panel) of delignified and refined MDF fibers at a Canadian Standard Freeness (CSF) of 650 mL. FIG. 33B shows an optical micrograph (left panel) and an SEM image (right panel) of delignified and refined MDF fibers at a Canadian Standard Freeness (CSF) of 450 mL.

FIG. 38A is the first part of Table 1 from Example 2. FIG. 38B is the second part of Table 1 from Example 2. Table 1. Shows the chemical compositions of p-TsOH fractionated poplar NE222 samples under different treatment conditions. The numbers in the parentheses are component yields based on component in the untreated NE222. [1] (Pxx, Txx, txx) stands for p-TsOH concentration in wt %, reaction temperature in ° C. and reaction duration in min. [2]Yields are based on xylan content in NE222. HMF in spent liquors were not detectable.

DETAILED DESCRIPTION

Figure 1:
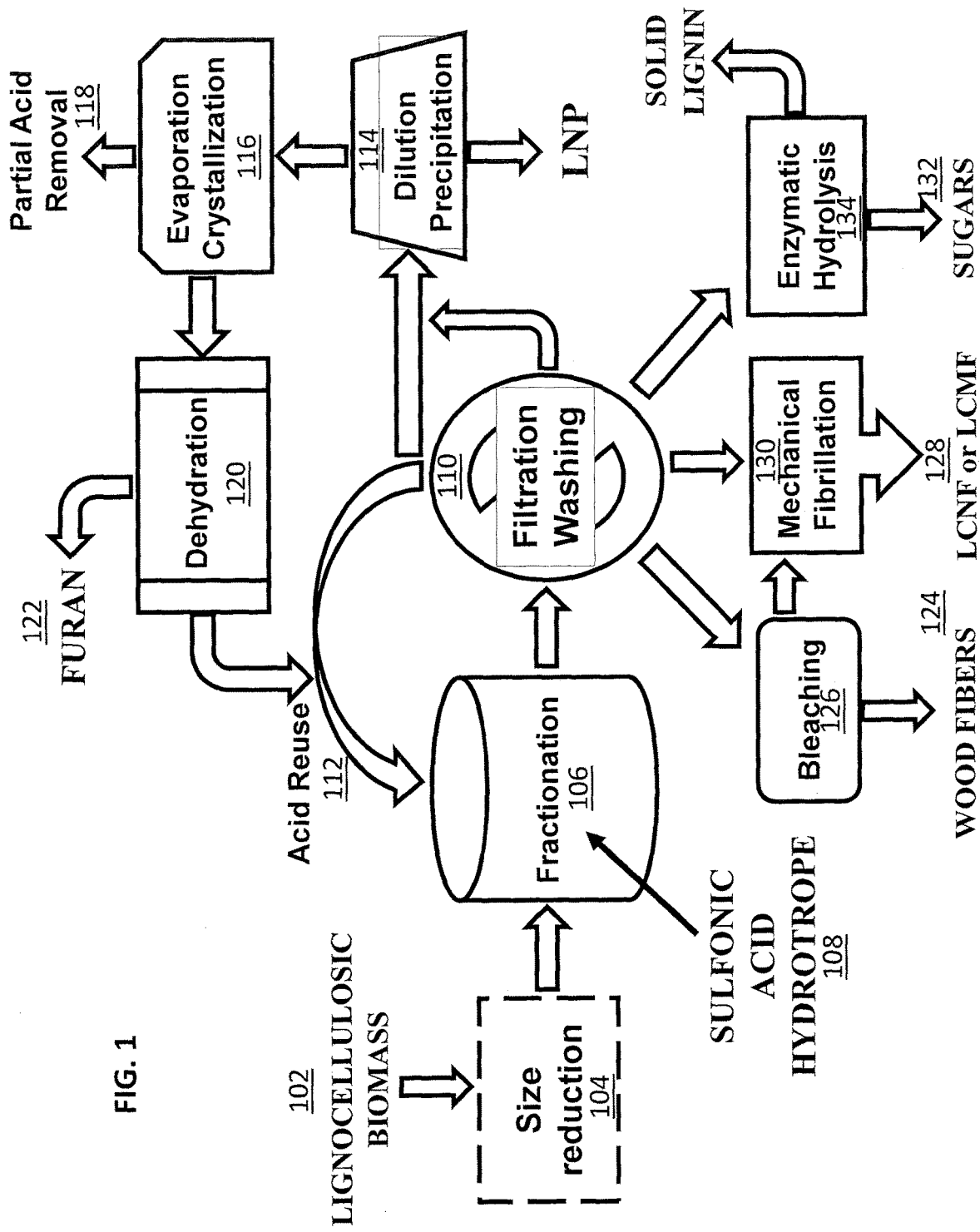
FIG. 1 is a flow chart showing one embodiment of a wood processing method that includes a lignocellulosic biomass fractionation using sulfonic acid hydrotropes.

Various embodiments of the inventions described herein are based, at least in part, on the discovery that certain organic solid acids have hydrotropic properties, and are capable of efficiently solubilizing hydrophobic lignin at low temperatures (below the boiling point of water) in a short period of time. As such, a low-energy, low-cost and efficient lignocellulosic biomass fractionation process can be carried out using these easily recyclable organic solid acids, which include p-toluenesulfonic acid (p-TsOH), in aqueous solution, at low temperatures and atmospheric pressures. The fractionation produces a solid fraction that contains mainly cellulose and some hemicelluloses and a liquid fraction that contains dissolved lignin and some hemicellulosic sugars. The solid fraction can be used with or without bleaching to produce wood fibers, and/or cellulose micro- or nanomaterials, and/or sugars (through hydrolysis), and/or valuable chemicals, such as furfural. The cellulose micromaterials and nanomaterials include lignocellulosic micro-fibrils (LC-MFs) or lignocellulosic nano-fibrils (LCNFs) with controllable lignin contents on their surfaces (e.g., coated via precipitation) or in their cellulosic matrices (containing native lignin) from the fractionated solids. The solubilized lignin in the liquid fraction can be separated as lignin nanoparticles through the precipitation of solubilized lignin by diluting the spent acid solution with water to a concentration below the minimal hydrotrope concentrations (MHC). The obtained lignin nanoparticles (LNPs) comprise oblate spheroids with tunable morphology and surface properties. Some embodiments of the LNPs have diameters ranging from, for example, 150~3000 nm and thicknesses ranging from, for example, 3~50 nm. The properties of the lignin LNPs can be tailored by controlling the pretreatment conditions of the biomass and the diluting factors of the spent acid solutions, as illustrated in the Examples.

Lignocellulosic Biomass:

As used herein, the term lignocellulosic biomass refers to materials from plant cell wall that primarily includes lignin and hemicelluloses, as well as cellulose. Lignocellulosic biomass may be, for example, wood, grasses, and agriculture crop stems or stalks. Wood biomass can be a hardwood or a softwood or a mixture thereof. The wood may be provided in milled or chip form. However, for the production of wood fibers, wood chips may be more suitable.

Lignocellulose Nanocrystals (LCNCs):

As used herein, the term LCNC refers to elongated rod-like crystalline lignin-containing cellulose nanoparticles. LCNCs comprise cellulose chains produced from lignocellulosic biomass via fractionation. LCNCs can be in the form of a single cellulose crystallite or a bundle of cellulose crystallites, and may or may not contain hemicelluloses. LCNCs are generally characterized by lengths in the range from about 60 to about 1000 nm; widths in the range from about 5 to about 50 nm; and corresponding aspect ratios in the range from about 1 to about 200.

Lignocellulose Nanofibrils (LCNFs):

As used herein, the term LCNF refers to long flexible fiber-like lignin-containing cellulose nanoparticles. LCNFs can be branched or unbranched and can take the form of a network of flexible fiber-like nanoparticles. LCNFs comprise cellulose, hemicellulose, and lignin. The fiber-like lignocellulose particles are generally characterized by lengths in the range from about 100 to about 5,000 nm; widths in the range from about 5 to about 200 nm; and corresponding aspect ratios in the range from about 2 to about 1,000.

Lignocellulose Fibers (LCFs):

As used herein, the term LCF refers to lignin-containing cellulose particles. LCFs comprise cellulose, hemicellulose, and lignin. LCFs are generally characterized by lengths in the range from about 0.05 to about 3 mm; widths in the range from about 5 to about 50 µm; and corresponding aspect ratios in the range from about 2 to about 500.

Lignocellulose Microfibers (LCMFs):

As used herein, the term LCMF refers to lignin-containing cellulose microparticles. LCMFs comprise cellulose, hemicelluloses, and lignin. LCMFs are characterized by lengths in the range from about 5 to about 100 μm; widths in the range from about 0.1 to about 10 μm; and corresponding aspect ratios in the range from about 2 to about 500.

Lignocellulosic Solid Residues (LCSR):

As used herein, the term LCSR refers to a solid material composed of LCFs, LCMFs, or a combination thereof. In the present methods, LCSRs are part of the solid material remaining after the biomass fractionation.

Lignin Nanoparticles (LNPs):

As used herein, the term LNP refers to lignin nanoparticles. LNPs can be in the form of single lignin macro molecule or aggregates of lignin macro molecules. LNPs are generally characterized by dimensions in the range from 1 nm to 10 μm (e.g., from 10 nm to 500 nm) and may have an oblate spheroid shape.

The lignocellulosic biomass fractionation methods utilize sulfonic acids, such as methenesulfonic acid, and, in some embodiments, aromatic sulfonic acids, such as p-toluenesulfonic acid, benzenesulfonic acid, xylenesulfonic acid, and mixtures of two or more thereof, or mixtures of one or more thereof with their salts.

One aspect of the present invention uses a concentrated organic sulfonic acid, rather than, or in addition to, sulfonic (aromatic) salts, to solubilize lignin for wood fractionation. With sulfonic aromatic acids, the process can be conducted at low temperatures using a very short reaction time. By way of illustration, various embodiments of the lignocellulosic biomass fractionation are carried out at temperatures of no greater than 100° C. This includes embodiments of the lignocellulosic biomass fractionation that are carried out at temperatures of no greater than 90° C. and further includes embodiments of the lignocellulosic biomass fractionation that are carried out at temperatures of no greater than 80° C. For example, the lignocellulosic biomass fractionation can be carried out at temperatures in the range from 30° C. to 85° C., including temperatures in the range from 50° C. to 85° C., and further including temperatures in the range from 60° C. to 80° C. However, temperatures outside of these ranges can be used, depending on the desired degree of lignin dissolution. By way of further illustration, various embodiments of the lignocellulosic biomass fractionation can be completed in a reaction time of 5 hours or less. This includes embodiments of the lignocellulosic biomass fractionation that are completed in a reaction time of 4 hours or less, 3 hours or less, 2 hours or less, and 1 hour or less. For example, the lignocellulosic biomass fractionation can be carried out for a reaction time in the range from 15 minutes to 90 minutes, including reaction times in the range from 20 minutes to 60 minutes. However, reaction times outside of these ranges can be used, depending on the desired degree of lignin dissolution. As used herein, the reaction time refers to the time between the onset of the solubilization of the lignin in the biomass by the sulfonic acid and the cessation of the lignin solubilization when the sulfonic acid concentration in the fractionation solution is brought below its minimal hydrotrope concentration. By way of illustration, the solubilization of lignin using p-TsOH can be terminated by decreasing the acid concentration to below about 11.5 wt. %.

In the lignocellulosic biomass fractionation solution, the sulfonic acid has a concentration above its minimum hydrotrope concentration, so that it solubilizes lignin, which is hydrophobic, in the fractionation solution. Generally, the sulfonic acid has a concentration that is significantly greater than the minimum hydrotrope concentration in order to enhance lignin solubilization. By way of illustration, in various embodiments of the lignocellulosic biomass fractionation method, the fractionation solution has a sulfonic acid (for example p-TsOH) concentration of at least 15% (or above MHC). This includes embodiments of the methods in which the fractionation solution has a sulfonic acid concentration of at least 50%, at least 60%, at least 65%, at least 70%, at least 75%, and at least 80%. For example, sulfonic acid concentrations in the range from about 50% to about 85%, including in the range from about 65% to about 80%, can be used. However, concentrations outside of these ranges can be used, depending upon the desired degree of lignin dissolution.

The lignocellulosic biomass fractionation process can solubilize the majority of the lignin in a lignocellulosic biomass sample without the need for an initial pulping to reduce the lignin content prior to the sulfonic acid treatment. In various embodiments of the lignocellulosic biomass fractionations, at least 10% of the lignin in the biomass is solubilized during the fractionation. This includes embodiments of the fractionations that solubilize at least 45%, at least 50%, at least 55%, at least 60%, at least 65%, at least 70%, at least 75%, at least 80%, and at least 90% of the lignin in the biomass. However, percentages of lignin solubilization outside of these ranges can also be achieved. The solubilization of the lignin can also be quantified in terms of grams of lignin dissolved per 100 g of solution. In some embodiments of the lignocellulosic biomass fractionation, at least 2 g lignin/100 g of solution is dissolved.

One aspect of the invention provides a low temperature and ambient pressure wood processing method that includes lignocellulosic biomass pre-treatment, followed by the lignocellulosic biomass fractionation and, optionally, post-fractionation processing that can be carried out for producing fibers, and/or LCNF or LCMF, and/or sugars, and/or LNP with recovery of acid, as schematically shown in FIG. 1. In a lignocellulosic biomass pre-treatment step, lignocellulosic biomass 102, such as wood, is size-reduced 104 using, for example, low mechanical energy input disk milling conducted at temperatures above lignin glass transition temperature. Additionally, lignocellulosic biomass, such as wood chips, can be fibrillated using, for example, mechanical fibrillation, in order to increase exposed lignin at the fiber surfaces prior to lignocellulosic biomass fractionation. Another pre-treatment step that can be included in the process is prehydrolysis using hot water to improve hemicellulose removal and delignification. The size-reduced, fibrillated, and/or prehydrolyzed lignocellulosic biomass is then fractionated 106 using a sulfonic aromatic acid, such asp-TsOH, as a hydrotrope 108 for the lignin in the biomass at a low temperature (for example, approximately 80° C. or lower) for a short time (e.g., 20 minutes to one hour). After subsequent filtration and, optionally, washing 110, the spent acid solution from the lignocellulosic biomass fractionation 106 can be cycled back to the fractionation and directly reused 112. After several runs, dissolved solids, such as lignin and sugars, accumulate in the spent acid solution. These may be removed to further reuse the acid. Dissolved lignin in the filtrate can be easily removed by precipitation initiated through dilution with water 114. The diluted spent liquor can then be reconcentrated to convert dissolved sugars, such as xylose, into furans, such as furfural, through dehydration (e.g., evaporation) 116 using the sulfonic aromatic acid in the liquor as a catalyst. Reconcentration can also facilitate the removal of excess sulfonic aromatic acid 118 from the system through crystallization 116 when desirable. The furans 122 can be separated through distillation and dehydration 120. The remaining acid solution can then be cycled back to reused in the lignocellulosic biomass fractionation 106. The separated and subsequently washed water-insoluble solids contain lignocellulosic solid residues (LCSRs), and lignocellulosic nanocrystals (LCNC). Optionally, the LCNCs can be separated from the LCSRs by dialysis. The LCSR, with or without separating LCNC, can be used for producing chemical pulp fibers such as dissolving pulps 124 after bleaching 126, lignocellulose micro and/or nanofibrils (LCMF and/or LCNF) 128 with mechanical fibrillation 130, or sugars 132 through (enzymatic) hydrolysis 134.

Another aspect of the inventions provides methods for the production of LCNCs, LCNFs, LCMFs, and/or wood fibers from fractionated water insoluble solids, as described above and illustrated in FIG. 1. As illustrated in Example 7, the relative amount of LCNFs or LCMFs produced can be controlled by the severity of biomass fractionation. As illustrated in Example 8, low severity fractionation conditions tend to favor the production of long LCNFs.

Another aspect of the inventions provides methods for the production of LNPs with controllable sizes and shapes directly from the spent liquor from the biomass fractionation simply by precipitation after water dilution, as illustrated in FIG. 1. Processing conditions that can be used to control the size and morphology of the LNPs include the rate at which the spent fractionation solution is diluted and the severity of the biomass fractionation reaction conditions. The pH of the solution can also be used to tailor LNP size, whereby changing the pH of the spent liquor from the biomass fractionation to a low value (e.g., ≤3) or a high value (e.g., ≥10) results in a larger LNP size.

Another aspect of the inventions provides methods for the production of valuable chemicals, such as furans (e.g., furfurals), from the dissolved sugars, as illustrated in FIG. 1.

As used in this disclosure, any concentrations that are provided as a percentage (%) refer to a weight percentage (wt %), unless otherwise indicated.

EXAMPLES

Materials Used p-TsOH was purchased from Sigma-Aldrich (St. Louis, Mo.). Poplar NE-222 (*Populus deltoides* Bartr. ex Marsh×*P. nigra* L.) were harvested from Hugo Sauer Nursery in Rhinelander, Wis., USA, and provided by the US Forest Service, Northern Research Station. The NE222 logs were debarked and chipped at the US Forest Service, Forest Products Laboratory. Douglas-fir (*Pseudotsuga menziesii*) wood chips were collected by Weyerhaeuser Company from a pulp mill in Washington State. The NE222 and Douglas-fir wood chips were ground to a 20-mesh size using a Wiley mill.

White birch logs were obtained from the US Forest Service, Rhinelander Experimental Forest, Northern Research Station. The logs were harvested in February 2016 and had breast height diameter of 6-8 inches. The logs were peeled in March 2016 and immediately chipped at the US Forest Service, Forest Products Laboratory. The chips were screened using 1¼" square holes. Oversized chips were re-chipped to increase recovery.

Another softwood feedstock originated from Timber Products in Yreka, Calif. The feedstock are residuals from a veneer operation and comprise predominantly ponderosa pine with a small percentage of sugar pine. During veneer processing, all logs were debarked. On-spec logs were peeled for veneer, while defective logs were sent to the byproduct chipper. After veneer peeling, the residual bolts were chipped in a whole log chipper. The outputs of the two chipper lines were then mixed and screened. The undersized particles were sent to particle board production, while the oversized particles were re-chipped. The Timber Products specification for the resulting residual chips is less than 1% bark.

Example 1: Wood Fractionation Using a Concentrated p-TsOH Solution

Concentrated p-TsOH aqueous solutions at desired mass concentrations were prepared using de-ionized (DI) water. For studies using Wiley milled poplar and Douglas-fir wood particles, 50 mL of a prepared acid solution was added into a 150 mL flask and heated to the preset reaction temperature on a heating plate. A 5 g oven dry (OD) quantity of wood particles was transferred into the flask. The flask was then placed on a shaker at 200 rpm. At the end of the preset reaction time (between 5-60 min), the reaction was terminated by adding an appropriate amount of DI water to dilute the concentration down to 40 wt %. The solids were separated from the liquor using vacuum filtration. The filtrate was collected to produce LNP through dilution. The solids were thoroughly rinsed using DI water until the pH of the rinse filtrate did not change. The final rinsed solids were collected for compositional analyses.

Example 2: Fractionated Solids of NE222

The chemical compositions of the original, as well as the chemically fractionated solids of NE222, were analyzed by the Analytical Chemistry and Microscopy Lab (ACML) at the US Forest Service, Forest Products Lab, as described previously (Davis 1998; Luo et al. 2010). As listed in Table 1, FIGS. 38A and 38B, concentrated p-TsOH solution was able to solubilize a substantial (up to 90.7%) amount of poplar NE222 (hard wood) lignin using a very short reaction time of approximately 30 min at a temperature 80° C. or lower. This amount of lignin removal is equivalent to chemical pulping that is often conducted at temperatures of 170° C. for 2 hours with fairly high alkali loadings of approximately 25% on wood. Dissolution of xylan was also substantial. Glucan loss, however, was minimal, especially at a temperature of 65° C. or lower. Using an extended reaction time of 60 min or longer can compensate for reduced reaction severity at low temperatures, e.g., 65° C., to achieve improved lignin and hemicellulose dissolution while maintaining a high glucan yield. Lignin condensation occurred at 80° C. with reaction times of 35 min or longer. To achieve desired fractionation, the reaction severity can be adjusted. This is demonstrated in Eqs. (1a, b) and (2a, b). This is important to the production of pulp fibers, and especially for dissolving pulp fibers which require high cellulose yield, good strength, and minimal lignin and hemicellulose content.

$$L_R = (1 - \theta' - \theta'_R)e^{-CDF} + \theta' \cdot e^{-f \cdot CDF} + \theta'_R \qquad (1a)$$

with $$CDF = \exp\left(\alpha' - \frac{E'}{RT} + \beta'C\right)C \cdot t \qquad (1b)$$

$$X_R = (1 - \theta - \theta_R)e^{-CHF} + \theta \cdot e^{-f \cdot CHF} + \theta_R \qquad (2a)$$

with $$CHF = \exp\left(\alpha - \frac{E}{RT} + \beta C\right)C \cdot t \qquad (2b)$$

where $L_R$ and $X_R$ are fractions of lignin and xylan retained on the water insoluble solids (WIS), respectively. $\theta'$ and $\theta$ are the fractions of bulk fast solubilization lignin and xylan, respectively, $\theta'_R$ or $\theta_R$ are the fractions of unsolubilized residue lignin and xylan, f' or f are the ratio of lignin or xylan solubilization between the slow and bulk fast lignin or xylan, $\alpha'$, $\alpha$ and $\beta'$, $\beta$ are adjustable parameters, E' and E are activation energy, R is the universal gas constant (8.314 J mol$^{-1}$ K$^{-1}$), T is temperature in kelvins, C is initial p-TsOH concentration in mol$^{-1}$, and t is dissolution time in min.

Figure 2A:
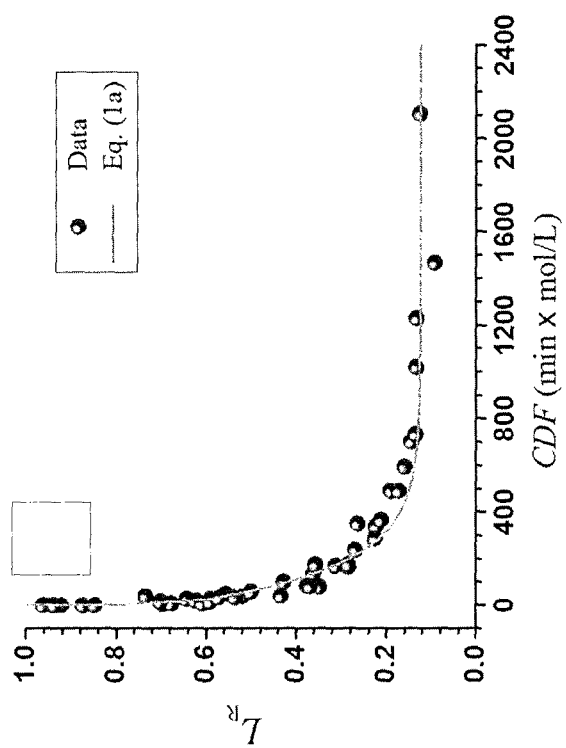
FIG. 2A is a graph of $L_R$, the fractions of lignin retained on the water insoluble solids of Example 2.
Figure 2B:
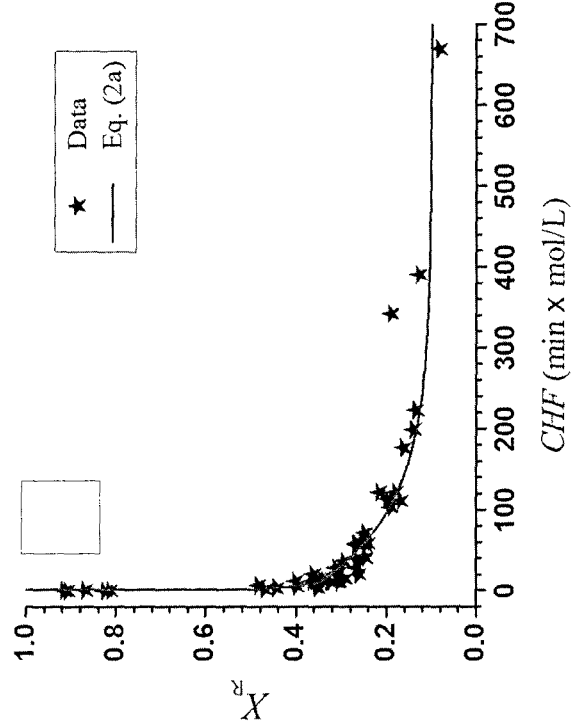
FIG. 2B is a graph of $X_R$, the fractions of xylan retained on the water insoluble solids of Example 2.

Eqs. (1) and (2) fit to the experimental data very well, as shown in FIGS. 2A and 2B. Furthermore, the dissolved carbohydrates in the spent liquor were mainly in the form of monomeric sugars. Degradation of xylose to furfural was minimal, less than 2% for most runs due to the rapid and low-temperature p-TsOH fractionation (Table 1 in FIG. 38A and FIG. 38B). Total xylan recovery from both the retained xylan and the dissolved xylose (not including oligomeric xylose in the spent liquor) were near 90% based on xylan content in untreated poplar NE222. Acetic acid concentration in the spent liquor was very low, at less than 1.5 g/L. These data demonstrate that p-TsOH fractionation can also efficiently recover hemicellulosic sugars.

Example 3: Fractionated Solids of Douglas-Fir

Fractionations were also carried out for Douglas-fir (softwood) as listed in Table 2. p-TsOH was less effective in solubilizing softwood lignin. A maximum of approximately 60% of Douglas-fir lignin was solubilized using a p-TsOH concentration of 80 wt % for 20 min at 80° C. An extended reaction time of 60 min caused lignin condensation, and slightly increased the residual lignin in the solids.

P75T65t35, P75T65t60, and P70T80t20. ((Pxx, Txx, txx) stands for p-TsOH concentration in wt %, reaction temperature in ° C. and reaction duration in min.)

Sugar production from fractionated Douglas-fir softwood was also carried out, but with slightly poorer performance compared with that from NE222.

Solubilized sugars in the spent acid solution, mainly hemicellulosic sugars, can be converted into furan, as discussed in Example 2 (Table 1 in FIGS. 38A and 38B).

Example 5: Dissolving Pulp Fiber Production from Poplar Wood

The fractionated solids have the potential for wood fiber production, especially dissolving grade pulp fibers, due to the substantial removal of hemicelluloses by the acid. One of the key measures of dissolving pulp is the pulp viscosity or DP. A separate set of fractionation experiments were conducted. Pre-hydrolysis using hot-water (HW) at 170° C. for 50 min (corresponding to a P-factor of 500) was applied to poplar wood chips to improve hemicellulose removal and delignification. Wood chips were used in these experiments, since Wiley milling shortens wood tracheid and therefore is not suitable for fiber production. The HW prehydrolyzed wood chips were then fractionated using a p-TsOH solution at 80 wt % concentration at 80° C. for 20 min based on the results shown in Table 1, FIGS. 38A and 38B. It was found that HW treatment did not improve lignin solubilization (Table 3). An 8-inch hand-driven disk mill (Andritz Sprout-Bauer Refiner, Springfield, Ohio) was also used to fiberize

TABLE 2

Chemical compositions of p-TsOH fractionated Douglas-fir solids under different treatment conditions. The numbers in the parentheses are component yields.

| Douglas-fir[1] | Solids yield (%) | Glucan (%) | Xylan (%) | Mannan (%) | Lignin (%) |
|---|---|---|---|---|---|
| untreated | 100 | 34.3 | 7.2 | 7.7 | 31.0 |
| P70T80t20 | 70.1 | 52.0 (106.4) | 3.8 (37.3) | 6.2 (56.0) | 32.6 (73.5) |
| P75T65t60 | 65.1 | 58.9 (111.9) | 3.9 (35.1) | 7.0 (58.7) | 31.6 (66.2) |
| P75T80t20 | 64.4 | 48.3 (90.7) | 3.3 (29.6) | 6.0 (49.6) | 30.7 (63.7) |
| P80T80t20 | 56.8 | 54.4 (90.1) | 3.3 (26.3) | 5.5 (40.7) | 25.2 (46.1) |
| P80T80t35 | 53.4 | 55.4 (86.4) | 2.5 (18.9) | 5.0 (35.1) | 24.9 (42.8) |
| P80T80t60 | 53.5 | 62.2 (97.1) | 2.7 (19.8) | 5.0 (34.4) | 26.3 (45.3) |

[1](Pxx, Txx, txx) stands for p-TsOH concentration in wt %, reaction temperature in ° C. reaction duration in min.

Example 4: Sugar Production from Fractionated Solids

Figure 3B:
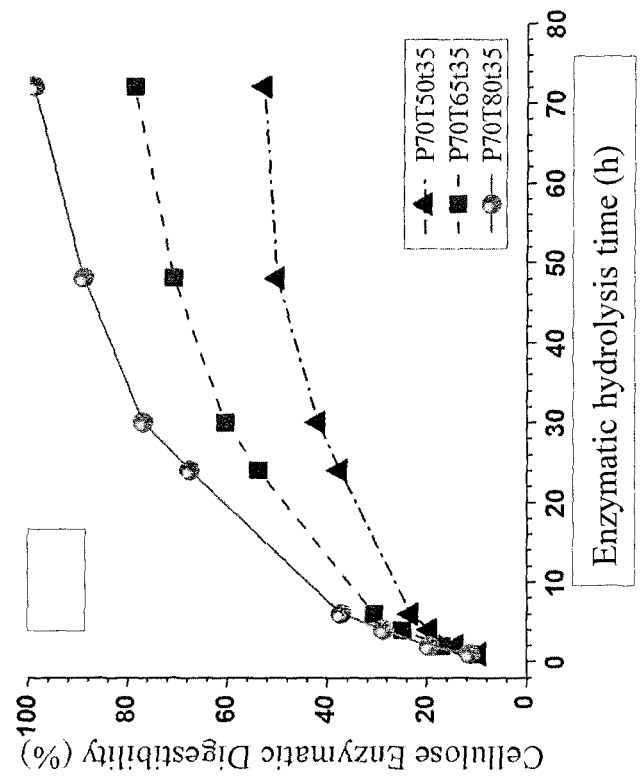
FIG. 3B is a graph of the cellulose enzyme digestibility for NE222 fractionated solids that were fractionated using a p-TsOH concentration of 70 wt % for 35 min at different temperatures.
Figure 3A:
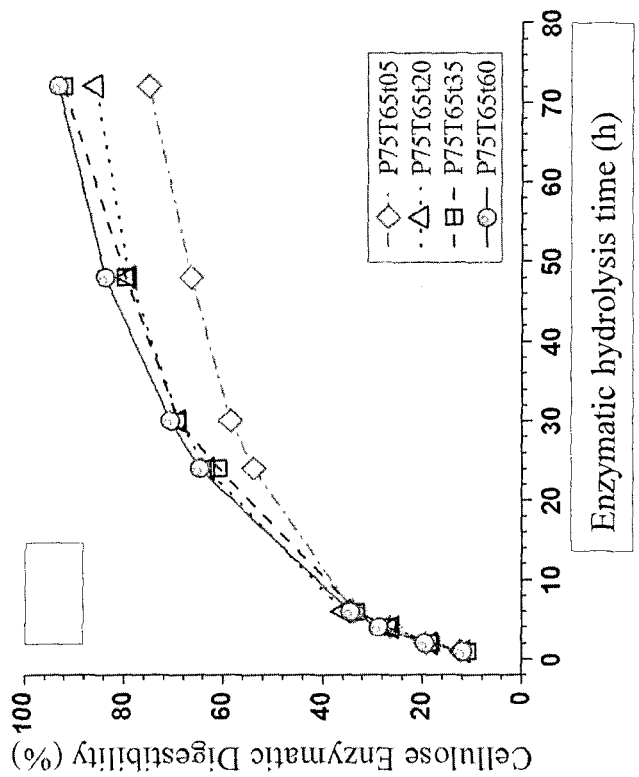
FIG. 3A is a graph of the cellulose enzyme digestibility for NE222 fractionated solids that were fractionated using a p-TsOH concentration of 75 wt % at 65° C. for different times.

The fractionated solids of NE222 were found to be enzymatically digestible. Therefore, the present methods using aromatic acids can be applied for sugar/biofuel production from lignocellulosic biomass using very low temperatures and at atmospheric pressure with short reaction times. When enzymatic hydrolysis was conducted using a commercial cellulase (CTec3) loading of 20 FPU/g glucan in acetate buffer of pH 5.5, cellulose enzymatic digestibility of over 90% was achieved, as shown in FIGS. 3A and 3B, for substrates produced at the more severe conditions, such as the wood chips to improve delignification in the subsequent treatment, with and without HW treatment, as shown in Table 3.

HW prehydrolysis, when applied alone, was relatively effective in solubilizing hemicelluloses (Table 3). When milling was applied, both the HW and non-HW samples behaved similarly; both allowed significant delignification and both types had similar hemicellulose contents (comparing Mill+P80T80t20 with HW+Mill+P80T80t20 in Table 3). This indicates that HW prehydrolysis is not necessary for the present methods. However, size reduction processes, such as milling, may be desirable for achieving a high degree of delignification.

TABLE 3

Chemical compositions of p-TsOH fractionated (at P80T80t20) NE222 wood chips with and without hot-water prehydrolysis and/or milling for dissolving pulp production. The numbers in the parentheses are component yields.

| NE222 [1] | Solids yield (%) | Glucan (%) | Xylan (%) | Mannan (%) | Lignin (%) |
|---|---|---|---|---|---|
| Untreated | 100.0 | 46.5 | 15.4 | 4.5 | 23.7 |
| HW | 93.2 | 49.4 (98.9) | 7.1 (43.2) | 1.6 (33.6) | 25.6 (100.0) |
| P80T80t20 | 75.6 | 60.4 (98.2) | 7.3 (35.7) | 2.8 (48.0) | 18.6 (59.1) |
| HW + P80T80t20 | 75.3 | 60.5 (97.9) | 6.1 (29.8) | 2.3 (38.5) | 20.0 (63.5) |
| Mill + P80T80t20 | 56.9 | 71.9 (87.9) | 4.4 (16.4) | 3.1 (39.5) | 10.8 (14.2) |
| HW + Mill + P80T80t20 | 54.2 | 73.4 (85.6) | 4.2 (14.7) | 3.0 (36.8) | 5.3 (12.0) |
| HW + P80T80t20 + Bleach | 51.0 | 84.5 (92.7) | 4.5 (14.9) | 2.3 (26.0) | 1.0 (2.0) |
| Mill + P80T80t20 + Bleach | 43.1 | 90.0 (83.4) | 4.2 (11.8) | 2.4 (22.7) | 0.2 (0.3) |
| HW + Mill + P80T80t20 + Bleach | 41.4 | 92.9 (82.6) | 3.6 (9.6) | 2.2 (20.5) | 0.2 (0.3) |

[1] HW stands for hot-water at 170° C. for 50 min. (Pxx, Txx, txx) stands for p-TsOH concentration in wt %, reaction temperature in ° C. and reaction duration in min.

Chlorite bleaching was applied to three p-TsOH (P80T80t20) fractionated solid samples: with HW only, with milling only, and with both HW and milling as listed in Tables 4 and 5. Bleaching entailed mixing 2 g dried solid sample, 65 mL of 75° C. DI-water, 0.5 mL of glacial acetic acid and 0.6 g of sodium chlorite in a beaker for 4 hours. Additional reagents, consisting of 0.5 ml of glacial acetic acid and 0.6 g of sodium chlorite, were added at 1, 2 and 3 hours. The resulting bleached pulp was washed by vacuum filtration with DI-water until the pH of the filtrate was close to neutral, and then dried at 105° C. The sample without milling (HW+P80T80t20+Bleach) contained a substantial amount of lignin, so the bleaching was repeated on a new sample using double quantities of sodium chlorite, which resulted in a relatively low lignin level. The two samples with milling had relatively low xylan contents of approximately 4% or less, and lignin contents of 0.2% after bleaching. The pulp viscosities of these three samples were between 360 and 430 (mL/g), as listed in Table 4, and are slightly lower than the range of 450-500 (mL/g) for typical dissolving pulp fibers. Careful examination of the data in Table 1 of FIGS. 38A and 38B, shows that a low reaction temperature can result in low glucan degradation, or less deploymerization of cellulose, which can be used to improve the viscosity of the resultant pulp. The reduced delignification, due to a lower temperature or low p-TsOH concentration, can be compensated for by using a longer reaction time such as 60 min (comparing P75T80t20 with P75T65t60).

TABLE 4

Bleached pulp viscosity and DP.

| NE222 | Intrinsic viscosity (mL/g) | DP |
|---|---|---|
| HW + P80T80t20 + Bleach | 427.5 ± 0.7 | 587.6 ± 1.1 |
| Mill + P80T80t20 + Bleach | 377.7 ± 0.5 | 512.4 ± 0.9 |
| HW + Mill + P80T80t20 + Bleach | 357.5 ± 0.7 | 482.1 ± 0.4 |

Another set of experiments was carried out to evaluate the feasibility of reducing acid concentration for dissolving pulp production using the same refined poplar fibers described above without HW pretreatment. As can be clearly seen from Table 5, a low p-TsOH concentration can be compensated for with a longer reaction. Both the pulp viscosity and xylan content after chlorite bleaching are suitable for dissolving pulp.

TABLE 5

Chemical composition and pulp viscosity of bleached poplar NE222 pulp delignified by p-TsOH.

| Sample Label[1] | Solids yield (%) | Viscosity (mL/g) | Glucan (%) | Xylan (%) | Mannan (%) | Lignin (%) |
|---|---|---|---|---|---|---|
| Poplar NE222 | | | 45.7 | 14.9 | 4.6 | 23.4 |
| P85T80t20 | 64.7 | | 70.3 | 5.7 | 3.2 | 8.8 |
| (post-bleaching) | 45.2 | 442 | 75.7 | 5.8 | 3.3 | 0.8 |
| P65T80t180 | 60.7 | | 71.4 | 4.3 | 3.0 | 12.4 |
| (post-bleaching) | 43.7 | 522 | 74.8 | 4.7 | 3.6 | 0.7 |

[1] (Pxx, Txx, txx) stands for p-TsOH concentration in wt %, reaction temperature in ° C. and reaction duration in min.

Example 6: Production of Dissolving Pulp from Birch Wood

To further evaluate p-TsOH fractionation for dissolving pulp production, birch wood chips were used that are used widely for pulp production and contained a minimal level of mannan. Medium density fiberboard (MDF) type fibers were produced from the birch wood chips in a 12" pressurized disk refiner (Sprout-Bauer, model 1210P, Muncy, Pa., USA) by pre-steaming the wood chips at 165° C. or steam pressure 0.62 MPa (105 Psia). The disk plate pattern was D2B505 with a gap of 7/1000 inches. The wood chip feeding rate was approximately 1 kg/min. The MDF process has three distinct features uniquely suited for this study: (1) low energy cost in fiberization by pre-steaming above the lignin glass transition temperature to initiate fiber separation in the middle lamella; (2) as a result, a major portion of the lignin is exposed on the resulting fiber surface, which should facilitate solubilization of lignin by p-TsOH; (3) minimal fiber cutting that can avoid unnecessary reduction of DP or pulp viscosity.

TABLE 6

Chemical compositions of p-TsOH fractionated birch MDF for dissolving pulp and LCNF production. The numbers in the parentheses are component yields (g/100 g wood).

| Birch MDF [1] | Solids yield (%) | Glucan (%) | Xylan (%) | Mannan (%) | Lignin (%) |
|---|---|---|---|---|---|
| Untreated | 100.0 | 38.7 ± 0.88 | 21.5 ± 0.02 | 1.9 ± 0.03 | 20.2 ± 0.67 |
| P50T80t20 | 56.66 | 59.2 ± 0.96 (33.6) | 15.0 ± 0.28 (8.5) | 2.4 ± 0.02 (1.3) | 16.0 ± 0.47 (9.0) |
| P65T80t20 | 54.15 | 62.0 ± 0.74 (33.6) | 14.0 ± 0.12 (7.6) | 2.6 ± 0.01 (1.4) | 11.6 ± 0.32 (6.3) |
| P75T80t20 | 53.76 | 65.3 ± 1.59 (35.1) | 12.6 ± 0.21 (6.7) | 2.3 ± 0.11 (1.2) | 9.5 ± 0.23 (5.1) |
| P80T80t20 | 51.31 | 67.7 ± 0.20 (34.7) | 12.2 ± 0.08 (6.2) | 2.50 ± 0.07 (1.3) | 7.2 ± 0.18 (3.7) |
| P85T80t20 | 52.39 | 67.6 ± 2.69 (35.4) | 11.2 ± 0.43 (5.8) | 2.2 ± 0.10 (1.2) | 8.0 ± 0.12 (4.2) |
| P80T65t60 | 53.12 | 65.9 ± 0.01 (35.0) | 13.3 ± 0.02 (7.1) | 2.9 ± 0.01 (1.5) | 9.1 ± 0.03 (4.8) |
| P80T65t60-bleached | 46.63 | 77.9 ± 2.07 | 13.6 ± 0.38 | 2.7 ± 0.26 | 1.1 ± 0.06 |

The washed fractionated solids of P80T65t60 were used for dissolving pulp production. It appeared that the hydrolysis time of 60 min was too short when the temperature was reduced to 65° C. resulting in a hydrolyzed sample with very high xylan and lignin content of over 13 and 9%, respectively. After bleaching, the sample still had an undesirably high xylan content, while lignin was reduced to approximately 1%. The viscosity of the bleached pulp was 392 mL/g with DP of 533. The xylan in the sample contributed to the low DP. A long reaction time would address the problem associated with high lignin and xylan contents as shown in Table 5.

Example 7: Production of Lignocellulosic Nanocrystals from Birch Wood

Figure 4C:
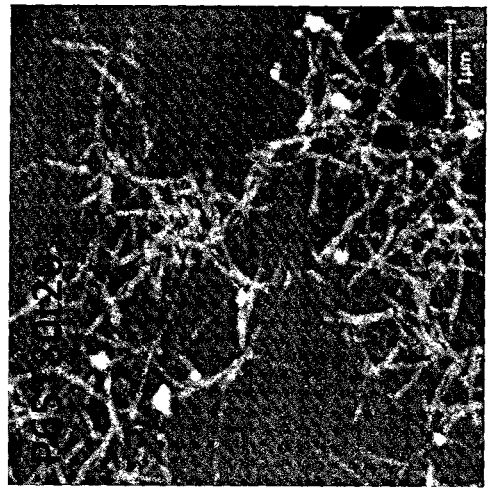
FIG. 4C is an AFM image of separated LCNC particles for sample P65T80t20 from Example 7.
Figure 4B:
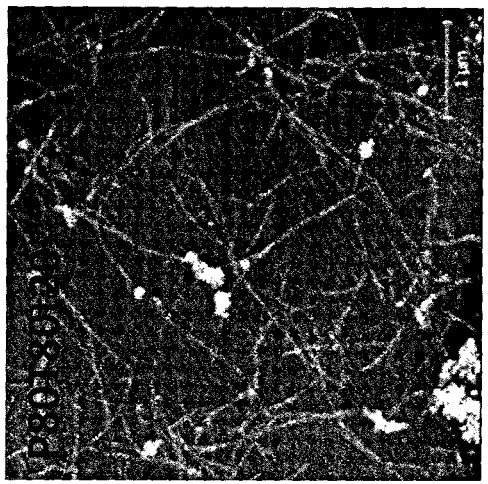
FIG. 4B is an AFM image of separated LCNC particles for sample P80T80t20 from Example 7.
Figure 4A:
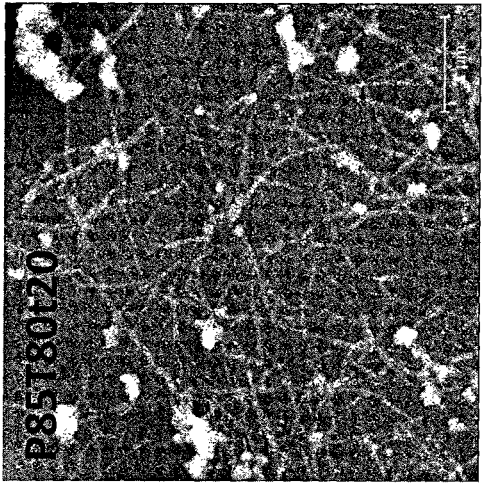
FIG. 4A is an atomic force microscope (AFM) image of separated LCNC particles for sample P85T80t20 from Example 7.
Figure 5:
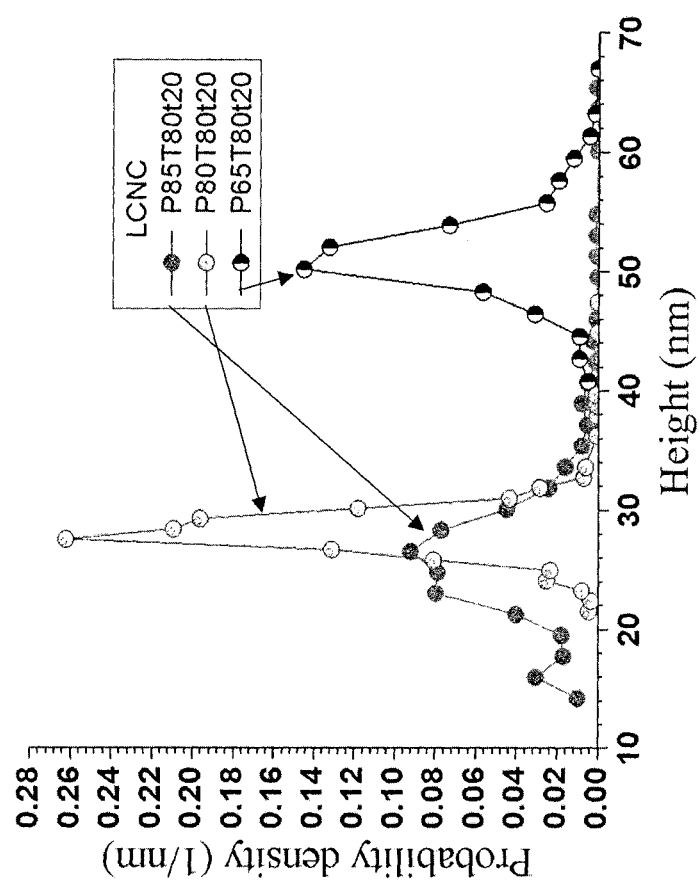
FIG. 5 shows the AFM height measured distributions for samples P85T80t20, P80T80t20, and P65T80t20 from Example 7.

The MDF fibers described in example 6 were used for the integrated production of LCNCs with LCNFs or LCMFs (depending on the extent of mechanical fibrillation and the severity of p-TsOH treatment). The MDF fibers were first fractionated using p-TsOH at several conditions using a fiber to acid solution ratio of 1:10. These conditions produced fractionated solids with varying lignin contents, as listed in Table 6. The hydrolyzed solids were thoroughly washed and centrifuged. The washed samples were dialyzed to separate LCNCs from the partially hydrolyzed LCSR. At neutral pH with conductivity between 1-2 μS/cm, the supernatant through centrifugation became turbid, suggesting the presence of LCNCs. The supernatant was then removed and further diluted to 0.01% for AFM imaging. As an example, the thoroughly washed hydrolyzed samples from P85T80t20, P80T80t20, P65T80t20 were dialyzed. The separated LCNC particles were fairly well dispersed, as shown by the AFM images in FIGS. 4A, 4B, and 4C. The AFM height measured distributions are shown in FIG. 5 with an average height of 26, 28, and 51 nm, respectively. The bimodal distribution of sample P85T80t20 was due to the free lignin nanoparticles as shown in FIG. 4A. The AFM images (FIGS. 4A-4C) showed very interesting morphology of the LCNCs with very long lengths of over 1 μm. The great height and long length indicated that the resultant material was CNC bundles.

Example 8: Production of Lignocellulosic Nanofibrils from Birch Wood

Figure 6A:
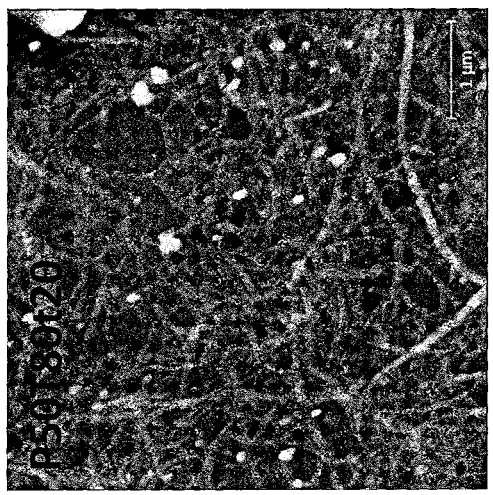
FIG. 6A is an AFM image of separated LCNF particles for sample P50T80t20 from Example 8.
Figure 6B:
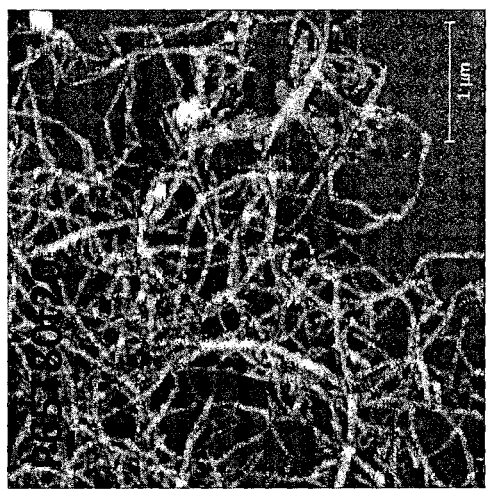
FIG. 6B is an AFM image of separated LCNF particles for sample P65T80t20 from Example 8.
Figure 6C:
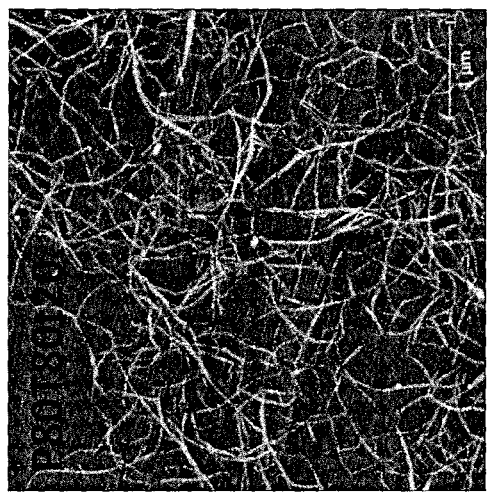
FIG. 6C is an AFM image of separated LCNF particles for sample P80T80t20 from Example 8.
Figure 7:
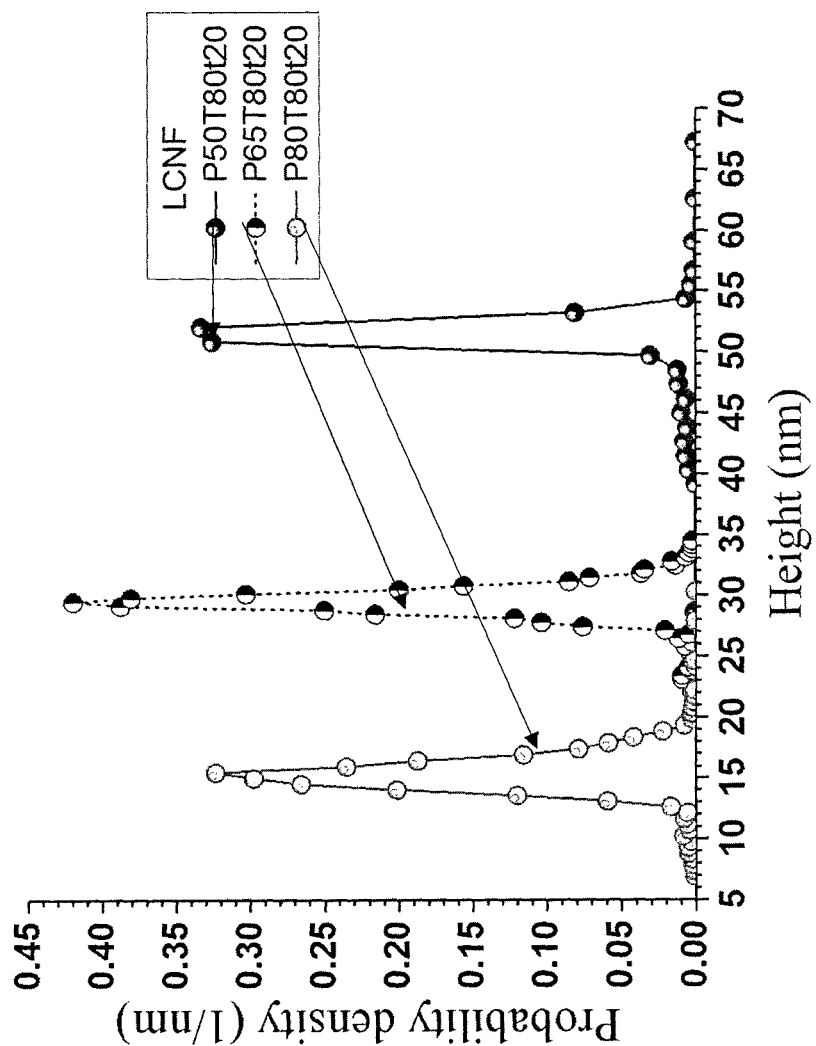
FIG. 7 is a graph showing AFM height measured distributions for LCNF samples P80T80t20, P65T80t20, and P50T80t20 from Example 8.
Figure 8C:
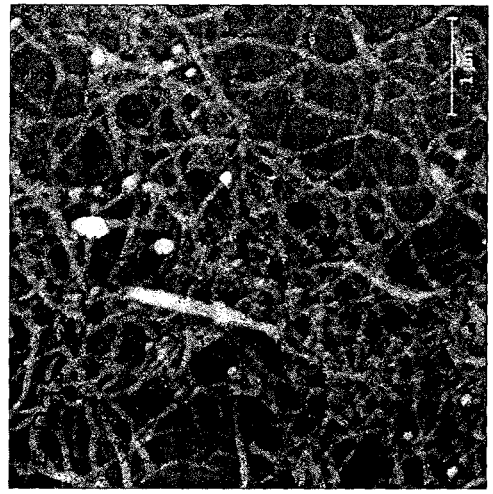
FIG. 8C is an AFM image of the LCNFs of Example 8 after five passes through the chamber of a microfluidizer.
Figure 8B:
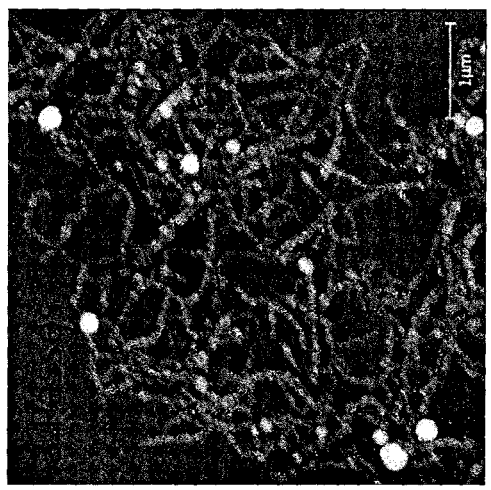
FIG. 8B is an AFM image of the LCNFs of Example 8 after three passes through the chamber of a microfluidizer.
Figure 8E:
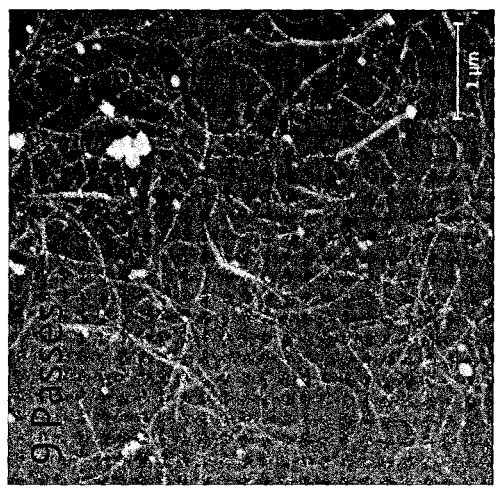
FIG. 8E is an AFM image of the LCNFs of Example 8 after nine passes through the chamber of a microfluidizer.
Figure 8A:
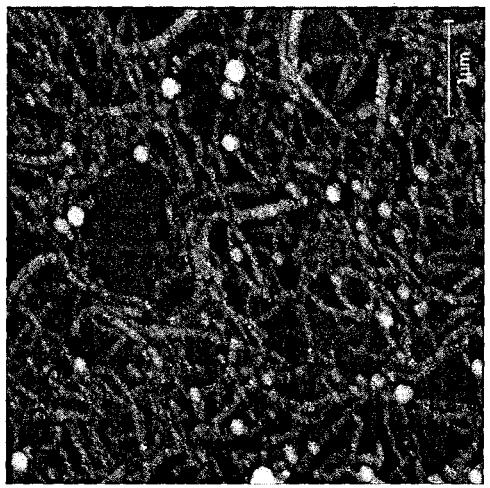
FIG. 8A is an AFM image of the LCNFs from P50T80t20 of Example 8 after one pass through the chamber of a microfluidizer.
Figure 8D:
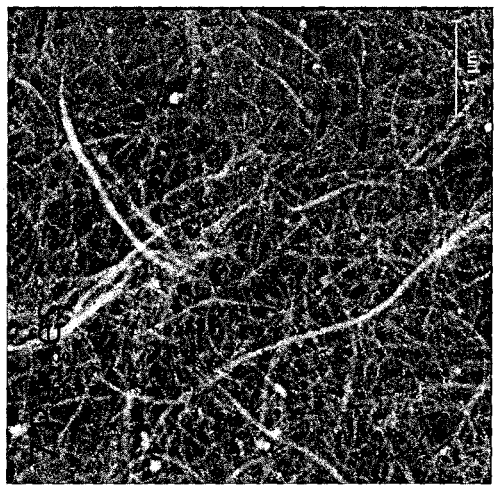
FIG. 8D is an AFM image of the LCNFs of Example 8 after seven passes through the chamber of a microfluidizer.

The LCSR, after separating LCNCs from the washed hydrolyzed WIS, was subsequently mechanically fibrillated to produce LCNFs or LCMFs, depending on the extent of fibrillation and the severity of acid hydrolysis. Optionally, especially under low-severity hydrolysis conditions for producing long and entangled LCNFs, LCNCs yield was low and the washed solids could be directly used for LCNF production without dialysis and separating LCNCs. The LCSR, or washed hydrolyzed WIS without separating LCNCs, was diluted with water to 1% suspensions and fibrillated using a microfluidizer (M-110EH, Microfluidics Corp., Westwood, Mass.). The suspensions were initially processed through a 200 μm chamber 3 times at 40 MPa, and then passed an additional 1-9 times through an 87 μm chamber at 120 MPa. Gelation was observed, suggesting that the solid suspensions became nanofibrils. Atomic Force Microscopy (AFM) images confirmed this as shown in FIGS. 6A, 6B, and 6C. These samples were produced using LCSR from P50T80t20, P65T80t20, and P80T80t20 after 5 passes through the 87 μm chamber, respectively. AFM measured fibril height probability density distributions from these three samples are shown in FIG. 7. The corresponding average heights of these three LCNF samples were 51.1, 29.4, 15.3 nm. All three LCNF samples showed remarkable uniformity in height as indicated by the narrow distributions (FIG. 7). The LCNF with the highest lignin content contained lignin nanoparticles (LNPs) clearly visible from the AFM image (FIG. 6). Increased fractionation severity clearly reduced lignin content (Table 6) and resulted in finer fibrils through mechanical fibrillation.

Figure 9:
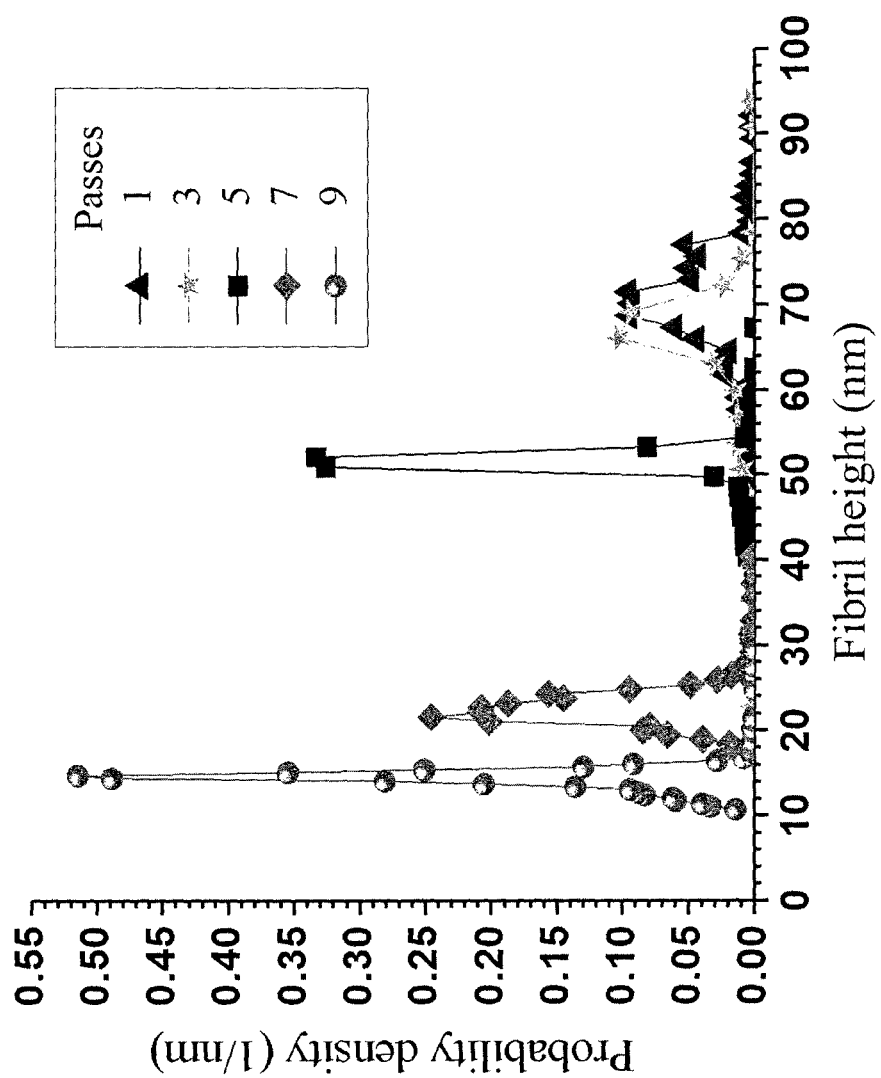
FIG. 9 shows the AFM height measured distributions for the LCNFs of FIGS. 8A-8E.

Increasing the extent of fibrillation also resulted in LCNFs with thinner diameters and less entanglement. The LCSR from the lowest severity run P50T80t20 was fibrillated using different passes. AFM measured fibril height distributions clearly showed the thinning of the fibril with more passes (FIGS. 8A, 8B, 8C, 8D, and 8E). The mean LCNF height was reduced from 70 to, 65.2, 51.1, 22.5, 14.3 nm after increasing the numbers of passes through the 87 μm chamber of the microfluidizer from 1 to, 3, 5, 7, and 9 (FIG. 9), respectively. Furthermore, the LCNFs became more uniform with more fibrillation.

Example 9: Production of Lignocellulosic Nanofibrils from Ponderosa Pine

Figure 10B:
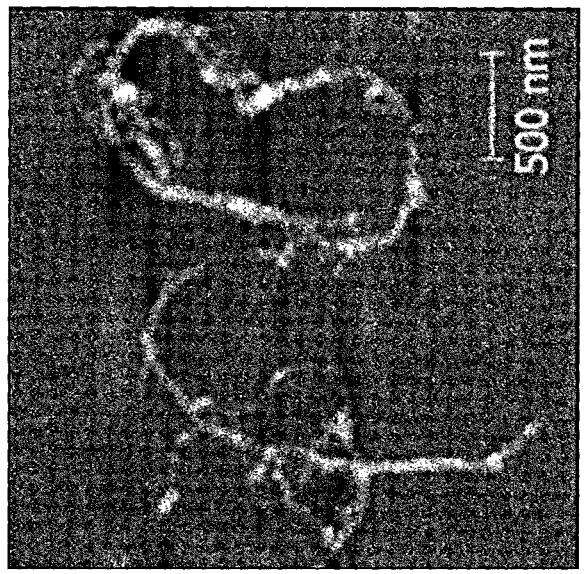
FIG. 10B is an enlarged image of the whisker-like cellulose nanofibrils of Example 9.
Figure 10A:
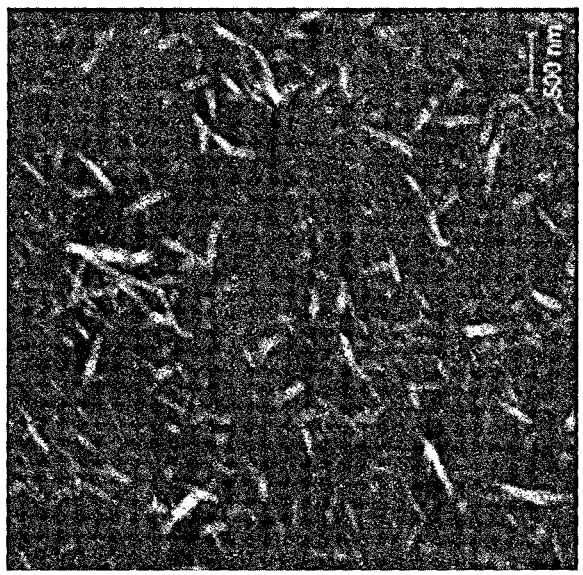
FIG. 10A is an image of the whisker-like cellulose nanofibrils of Example 9.
Figure 11:
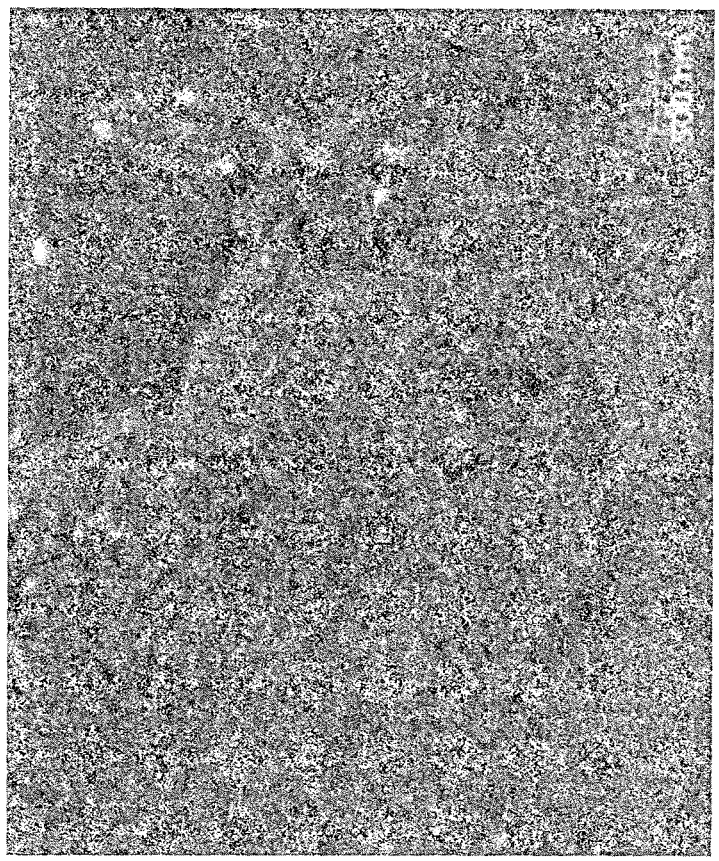
FIG. 11 is another image of the whisker-like cellulose nanofibrils of Example 9.

Ponderosa pine, a softwood, was also used to produce LCNFs. Ponderosa pine MDF fibers were produced with chips from Yreka, Calif. using the same 12" pressurized disk refiner and under the same conditions as described in Example 6. The MDF fibers were then treated using a p-TSOH solution of 80 wt % concentration at 80° C. for 20 min, or P80T80t20. The acid hydrolyzed sample was washed and 100 g in an oven dry (OD) base of the washed sample was processed in a Supermasscolloider (Model: MKZA6-2, Disk Model: MKGA6-80#, Masuko Sangyo Co., Ltd, Japan). The milling consistency was 2%, and the time was 60 min in the Supermasscollioder (SMC). As shown in FIG. 10, whisker-like cellulose nanofibrils were obtained. Unlike microfluidization, however, SMC produced a non-uniform cellulose nanofibril distribution, as indicated by the presence of the long fibrils shown in FIGS. 10A and 10B. However, when the SMC samples were subjected to two passes of microfluidization, all particles became very short whisker-like material as shown in FIG. 11.

Example 10: Production of Lignin Nanoparticles from Spent Liquor

Figure 12:
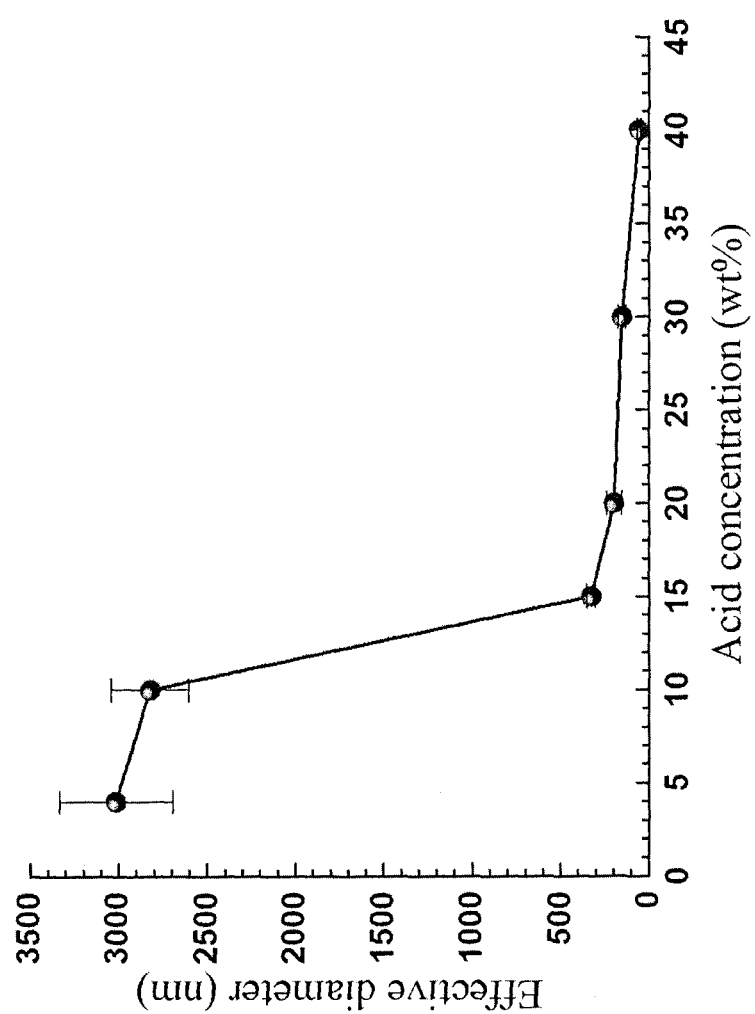
FIG. 12 is a graph showing lignin particle sizes measured by dynamic light scattering in a spent liquor at different acid dilution ratios, as described in Example 10.

The results in Tables 1 and 2 demonstrated that a substantial amount of wood lignin was solubilized, especially for poplar NE222 (hardwood). It was found that the solubilized lignin could be precipitated after diluting the aqueous spent liquor with additional water because p-TsOH is a hydrotrope. The critical acid concentration at which lignin precipitation occurred was monitored by dynamic light scattering (DLS) using a zeta potential analyzer (Nanobrook Omni, Brookhaven Instruments, Holtsville, N.Y.). The results from precipitating spent liquor of poplar NE222 at P75T80t20 are presented here. The DLS measured effective lignin particle sizes in the spent liquor at different dilution ratios, or equivalently the p-TsOH concentrations, are shown in FIG. 12. The results show that lignin precipitation was minimal at p-TsOH concentration ≥15%, as indicated by the very small measured particle size of less than 300 nm, as well as the minimal increase in size with dilution from the initial high concentration. The measured particle size rapidly increased to approximately 3000 nm when the spent liquor was diluted to a 10% concentration. The increase in particle size was not substantial with further dilution to below 4% concentration.

The spent liquor samples at the different dilution ratios were centrifuged at 3000 g for 10 min. Lignin precipitation was minimal at p-TsOH concentration of 20 wt % and higher. Precipitation increased substantially with dilution and the supernatant changed from highly opaque to clear. Therefore, the solubilized lignin could be readily recovered simply through dilution with water. The lignin recovery yield varied with dilution ratio. These results indicate that near full recovery can be achieved at p-TsOH concentration of approximately 4%.

Figure 13:
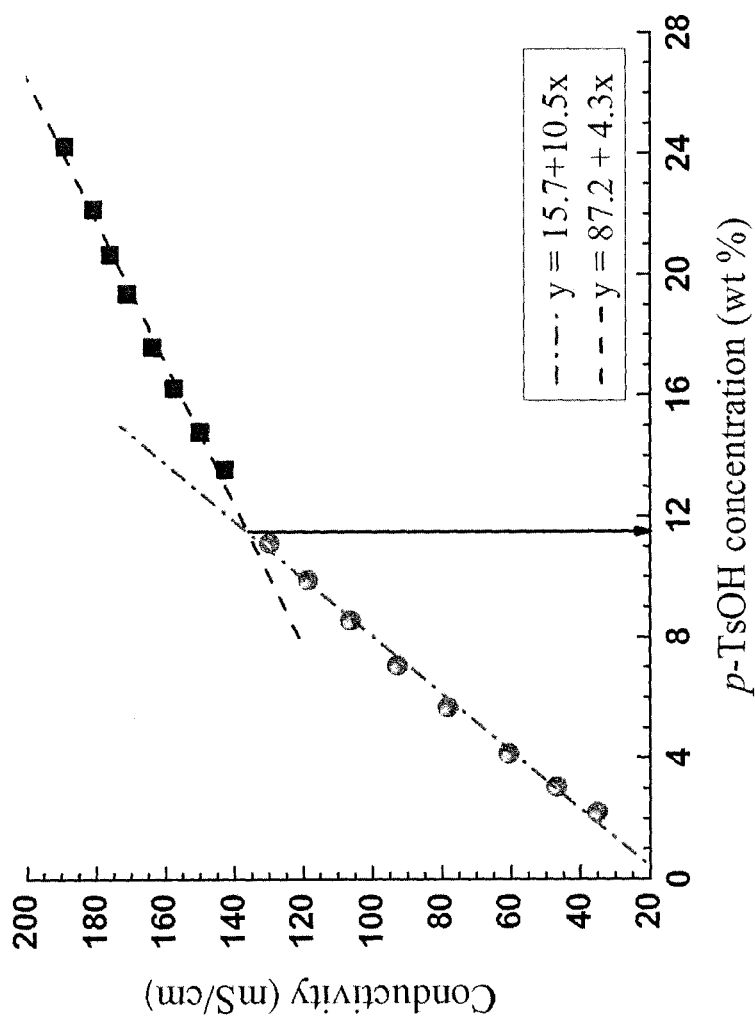
FIG. 13 is a graph of conductivity measurements versus concentration for aqueous p-TsOH solutions, as described in Example 10.

Early studies on hydrotropes (Balasubramanian et al. 1989; Hatzopoulos et al. 2011) indicated the existence of a minimal hydrotrope concentration (MHC), also called critical aggregate concentration (CAC), where hydrotropy is exhibited, i.e., below MHC lignin solubility disappears. Conductivity measurements were used for estimating the MHC. As shown in FIG. 13, the transition point in the measured conductivity of the diluted p-TsOH aqueous solution was at 11.5 wt %, suggesting MHC or CAC=11.5 wt %. This means that when the concentrated p-TsOH solution was diluted below 11.5 wt %, self-association disappeared. The solubility of lignin in the solution was impaired, resulting in precipitation.

Example 11: Characterization of Lignin Nanoparticle Size

The spent liquor at 40 wt % from dissolving poplar wood at P75T80t20 was diluted to 10 wt %, below the p-TsOH minimal hydrotrope concentration of 11.5 wt %. 10 mL of the diluted spent liquor was centrifuged at 3000 g for 10 min to precipitate the dissolved lignin. 7.5 mL of DI water was added back to further dilute the spent liquor top-TsOH concentration of approximately 2 wt %. Almost all dissolved lignin was precipitated through centrifugation. This was due to the strong ionic strength, which compressed the double electric layer on the surface of suspended lignin particles, making the lignin particles aggregate to precipitate out under the centrifugation force. Most of the ions were removed through further centrifugation and removing supernatant (or acid) followed by dilution, which resulted in a suspension with a p-TsOH concentration of 0.4 wt %, centrifugation with 3000 g for 10 min was unable to precipitate the charge particles due to the strong electrostatic repulsions among them, resulting in a turbid supernatant. This turbid supernatant exhibited a significant Tyndall effect; i.e., a red laser beam was visible in the direction perpendicular to its incident direction due to light scattering of very small particles. This showed that the dispersion was an aqueous sol, or colloidal system, that contained nanoparticles of lignin or LNPs.

Figure 14:
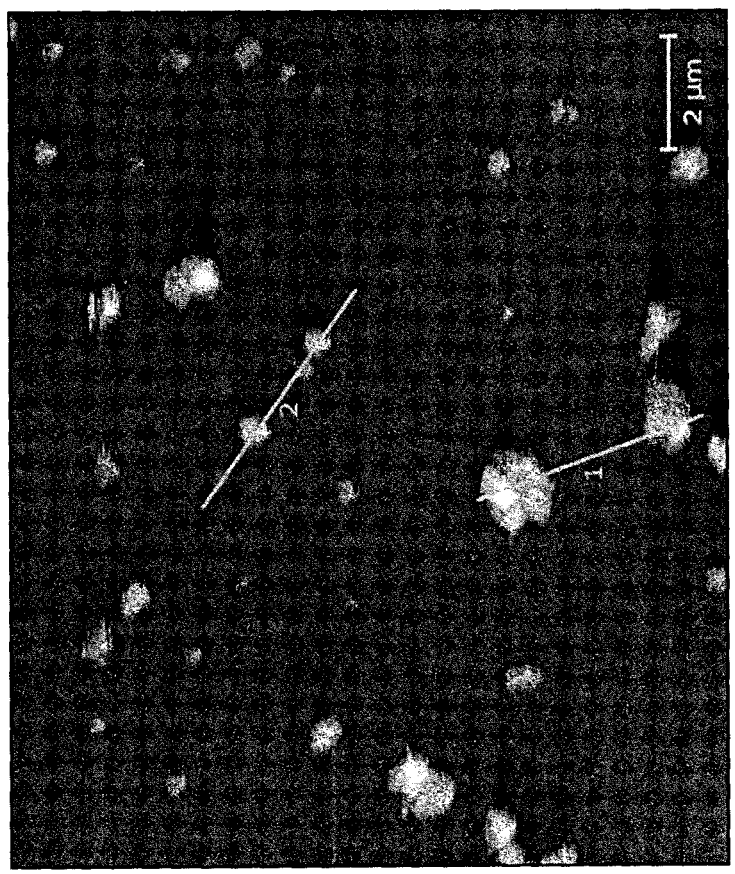
FIG. 14 is an AFM topographic image of the lignin particles of Example 11 deposited on a fresh mica sheet.
Figure 15:
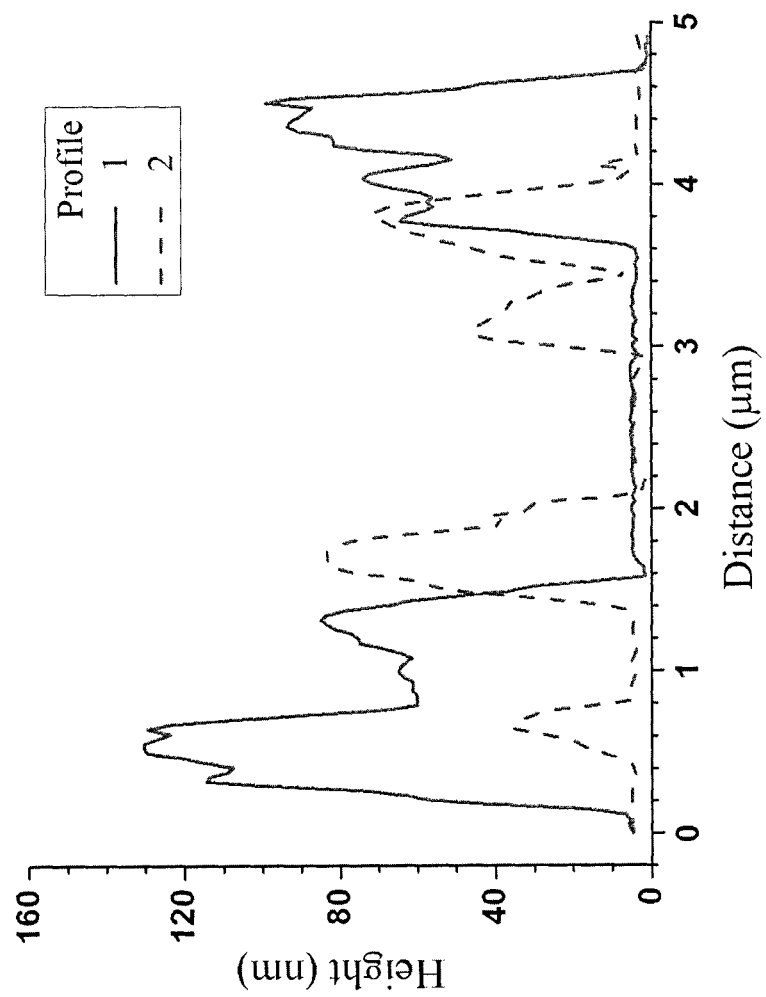
FIG. 15 is a graph showing the height profile of the lignin particles of FIG. 14.

The turbid supernatant and precipitate after the third centrifuge step were thoroughly mixed back together to examine all the lignin particles in the diluted spent liquor. An AFM topographic image of the resultant whole diluted suspension deposited on a fresh mica sheet is shown in the FIG. 14. The image confirmed nanoscale lignin particles formed through self-assembly of dissolved lignin after dilution. The sizes of the lignin nanoparticles ranged from 100 nm to 1 micrometer. Aggregates could be observed as shown by the multiple peaks in profile 1 in FIG. 15 corresponding to line 1 in FIG. 14. Less aggregated particles are observed from AFM height scanning profiles indicated by the separated single peaks in profile 2 (dashed line in FIG. 15), which correspond to line 2 in FIG. 14; and the diameter and thickness were determined to be approximately 500 and 50 nm, respectively. This suggests that the resultant LNPs were oblate spheroids.

Figure 17:
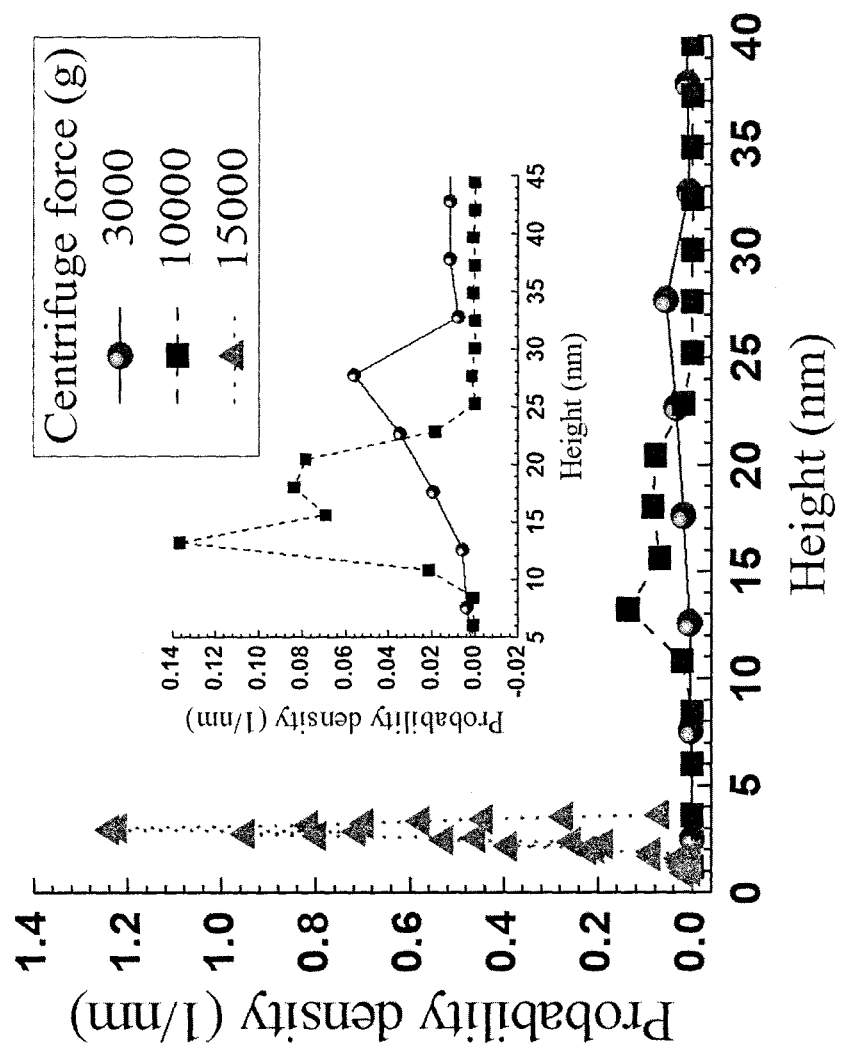
FIG. 17 is a graph of AFM height measurements of the LCNF samples of FIGS. 16A-16C.

The mixed diluted spent liquor was centrifuged at different speeds, after which the turbid supernatant was examined by AFM. Larger particles were precipitated during centrifugation, while only smaller particles remained in the supernatant. After air drying the supernatant on a mica plate, the sample obtained from centrifugation at 3000 g for 10 min contained lignin particle aggregates with lateral size of approximately 600 nm, as shown in FIG. 16A. Increasing centrifuge speed to 10000 g or higher, removed additional aggregates and large particles, resulting in relatively uniform and small LNPs in the supernatant as shown in FIGS. 16B and 16C. Typical LNP lateral sizes are approximately 200 and 50 nm at 10000 g and 15000 g, respectively. These results indicate that the diluted spent acid liquor contained lignin particles from tens of nanometers to approximately 1 micron. Furthermore, the large particles can be separated through centrifugation. AFM height measurements of the three supernatant samples are presented in FIG. 17. The heights are much smaller than their lateral dimensions. This shows that the LNPs were oblate spheroid nanoparticles with aspect-ratios (lateral or diameter:heights or thickness) of approximately 20, based on the results presented in FIGS. 16 and 17.

Example 12: Control of Lignin Nanoparticle Size and Surface Charge

Figure 18:
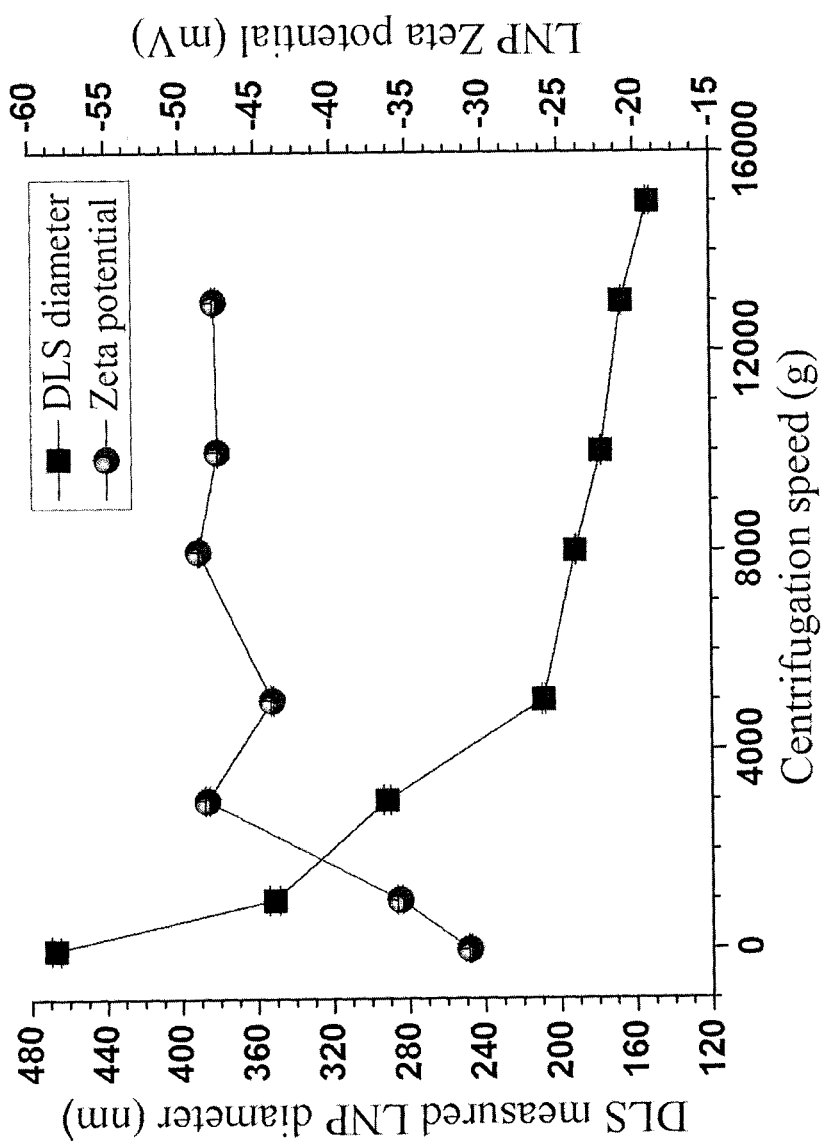
FIG. 18 is a graph of LNP particle size measured by dynamic light scattering as a function of centrifugation speed.

Particle charge is a critical property to particle dispersion and colloidal characteristics. The spent liquor from P75T80t20 at 40 wt % was quickly diluted to 10 wt % and then dialyzed to approximately pH 4.5. The average zeta-potential of the LNPs in the dialyzed sample was approximately −30 mV. Centrifugation can remove large particles in a suspension resulting in a supernatant that contains smaller particles, as discussed previously. This is clearly shown in FIG. 18 as measured by DLS of the LNPs in the diluted spent acid liquor. Removing large particles may also have facilitated particle dispersion in water, since the zeta potential increases from approximately −30 mV to −45 mV for the remaining LNPs in the supernatant after removing large particles using centrifugation at 3000 g (or higher) for 10 min (FIG. 18).

Figures 19A, 19B:
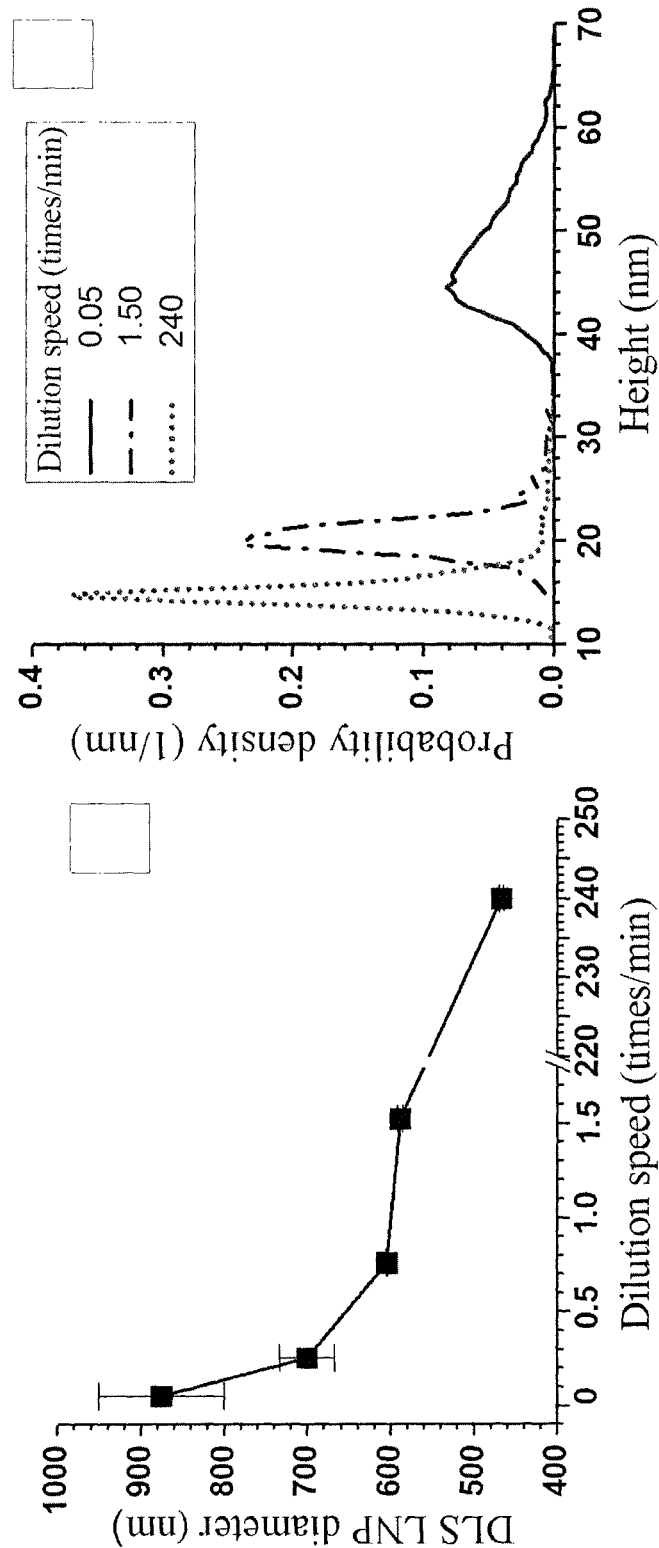
FIG. 19A is a graph of LNP particle size measured by dynamic light scattering as a function of dilution speed for the LNPs of Example 12.
FIG. 19B is an AFM height measurement of the LNPs of FIG. 19A at different dilution rates.
Figure 20C:
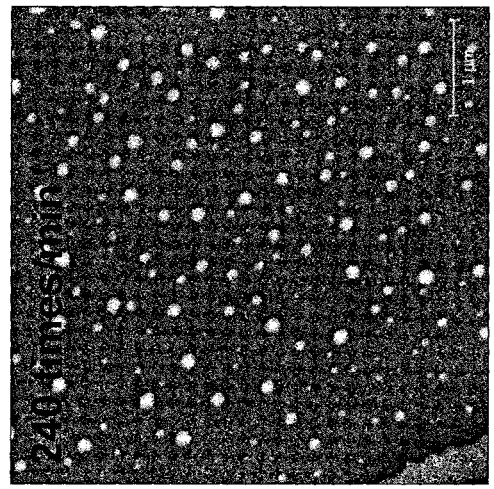
FIG. 20C is an AFM image of lignin aggregates formed using a dilution time/min of 240.
Figure 20B:
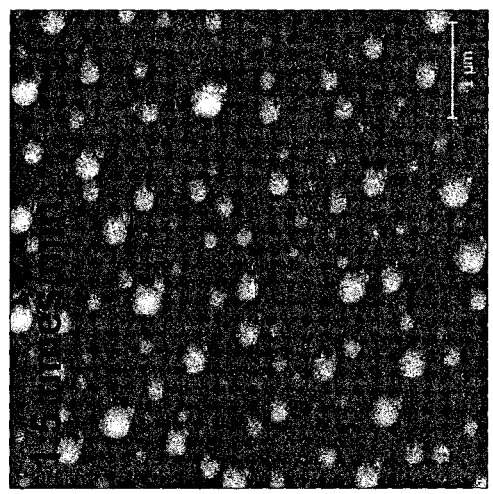
FIG. 20B is an AFM image of lignin aggregates formed using a dilution time/min of 1.5.
Figure 20A:
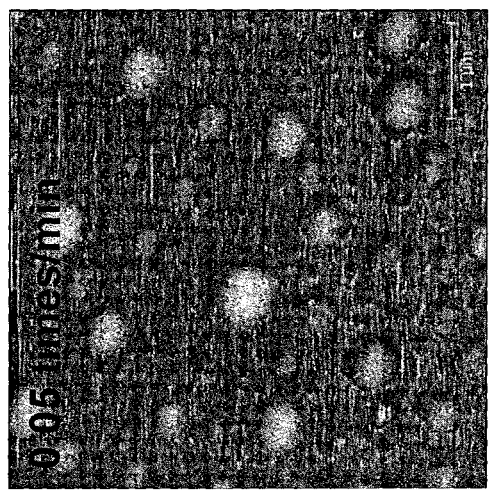
FIG. 20A is an AFM image of lignin aggregates formed using a dilution time/min of 0.05, as described in Example 12.

The speed of dilution was found to affect LNP morphology. 5 g of the spent liquor at a p-TsOH concentration of 40% from the run P75T80t20 was mixed with 15 g DI water using a peristaltic pump at four different flow rates of 0.19, 0.95, 2.85 and 5.71 mL/min, respectively. The dilution speed was determined in terms of dilution times/min. An extremely fast dilution speed of 240 times/min was achieved by manually adding 15 g of water into the flask in 1 second. A final dilution ratio of 4 times was applied in all dilution experiments to p-TsOH concentration of 10 wt %. The dissolved lignin aggregates when the spent liquor is diluted to 10 wt % (below the MHC of 11.5 wt %). The speed of dilution or water mixing with the hydrotropep-TsOH during dilution affected lignin aggregation and dispersion. DLS measured LNP size decreased rapidly from approximately 900 nm, when the spent acid liquor was diluted to 10 wt % at the slowest rate, to 450 nm when diluted at the fastest rate, as shown in FIG. 19A. The DLS measured particle sizes were also qualitatively in agreement with the lateral diameters from AFM images (FIGS. 20A, 20B, and 20C). The increase in particle size was a direct result of dissolved lignin aggregation during dilution. Apparently, a slow dilution increased the dissolved lignin aggregation time and resulted in a larger DLS particle size than that obtained via a fast dilution. A longer aggregation time also resulted in the increase in the thickness of lignin aggregates, as confirmed by the AFM measured height distributions (FIG. 19B).

Figure 21B:
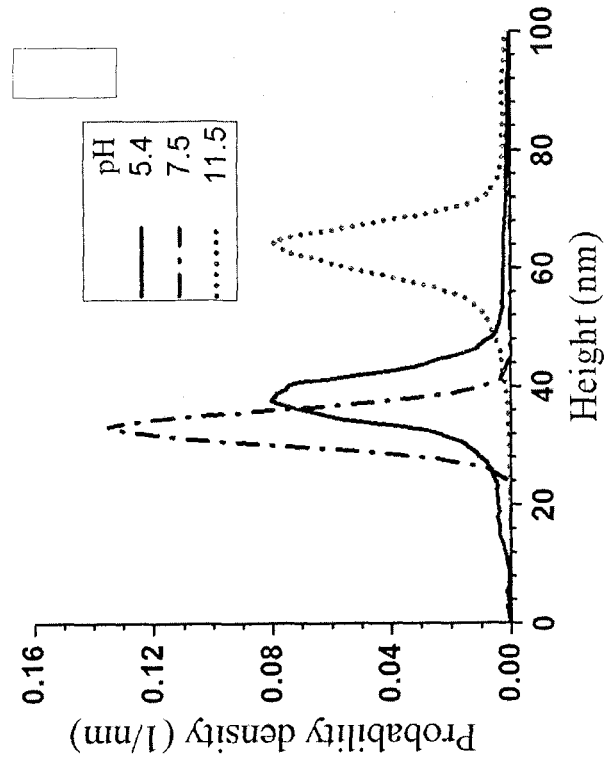
FIG. 21B is a graph of AFM height measurements for the LNPs of FIG. 21A at different pH values.
Figure 21A:
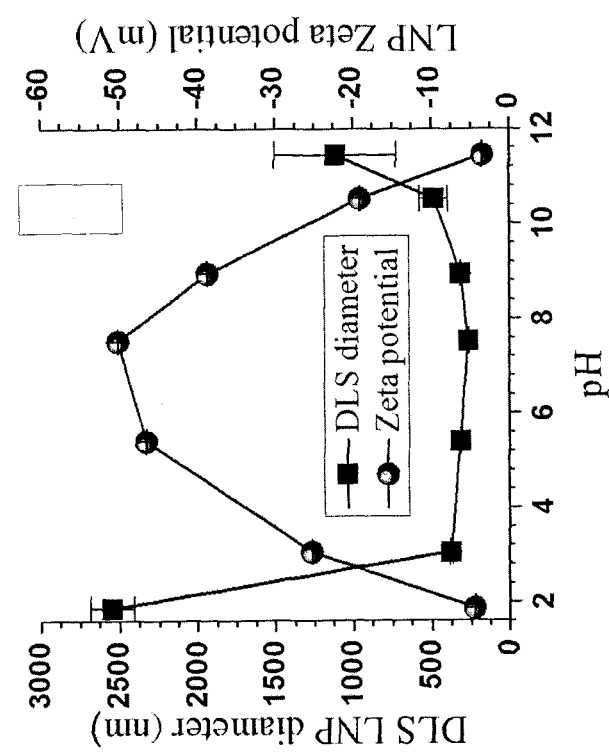
FIG. 21A is a graph of LNP particle size and zeta potential for the LNPs of Example 12 as a function of solution pH.
Figure 22C:
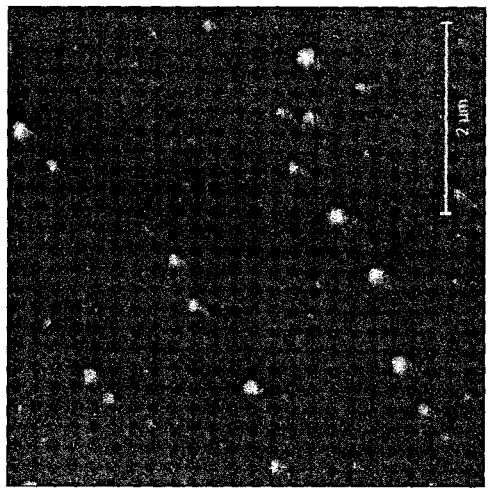
FIG. 22C is an AFM image of the LNCs of Example 12 at a solution pH of 5.4.
Figure 22B:
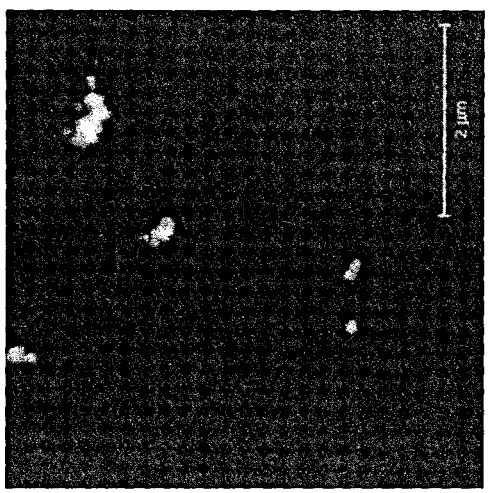
FIG. 22B is an AFM image of the LNCs of Example 12 at a solution pH of 7.5.
Figure 22A:
FIG. 22A is an AFM image of the LNCs of Example 12 at a solution pH of 11.5.

For negatively charged LNPs, pH and ionic strength can affect their aggregation and charge. The effects of pH were investigated by spiking a solution of NaOH at 0.1 mol/L or with HCl at 0.1 mol/L into the lignin supernatant from centrifuging at 3000 g for 10 min and subsequently dialyzing to pH 4.5. DLS measured LNP mean particle sizes were relatively stable between pH 3.0-10 with a slight reduction in size as pH increased to approximately 7.5, followed by a slight size increase as the pH increased to 10, as shown in FIG. 21A. Reducing pH below 3 or increasing pH above 10 resulted in a rapid increase in DLS measured LNP size. This was also verified by AFM imaging as shown in FIGS. 22A, 22B, and 22C. The results shown in FIG. 21A show that pH is a good parameter to control LNP size. Furthermore, within a wide range of pH 3-10, mean DLS LNP size was fairly constant. This is important for LNP applications.

Zeta potential shows the opposite trend of LNP size with respect to pH. With increasing pH, the zeta potential increased (absolute value) rapidly from about −4 mV to approximately −50 mV at about pH 8, and then decreased rapidly as the pH rose to near 12. The maximal zeta potential corresponded closely to the smallest LNP size (FIG. 21A), showing that electrostatic repulsion played a major role in lignin particle aggregation. The results also indicated that a zeta potential of −25 mV or higher (absolute value) was desirable to avoid substantial lignin particle aggregation, as shown by the rapid increase in LNP size at zeta potential below 25 mV.

Figures 23A, 23B:
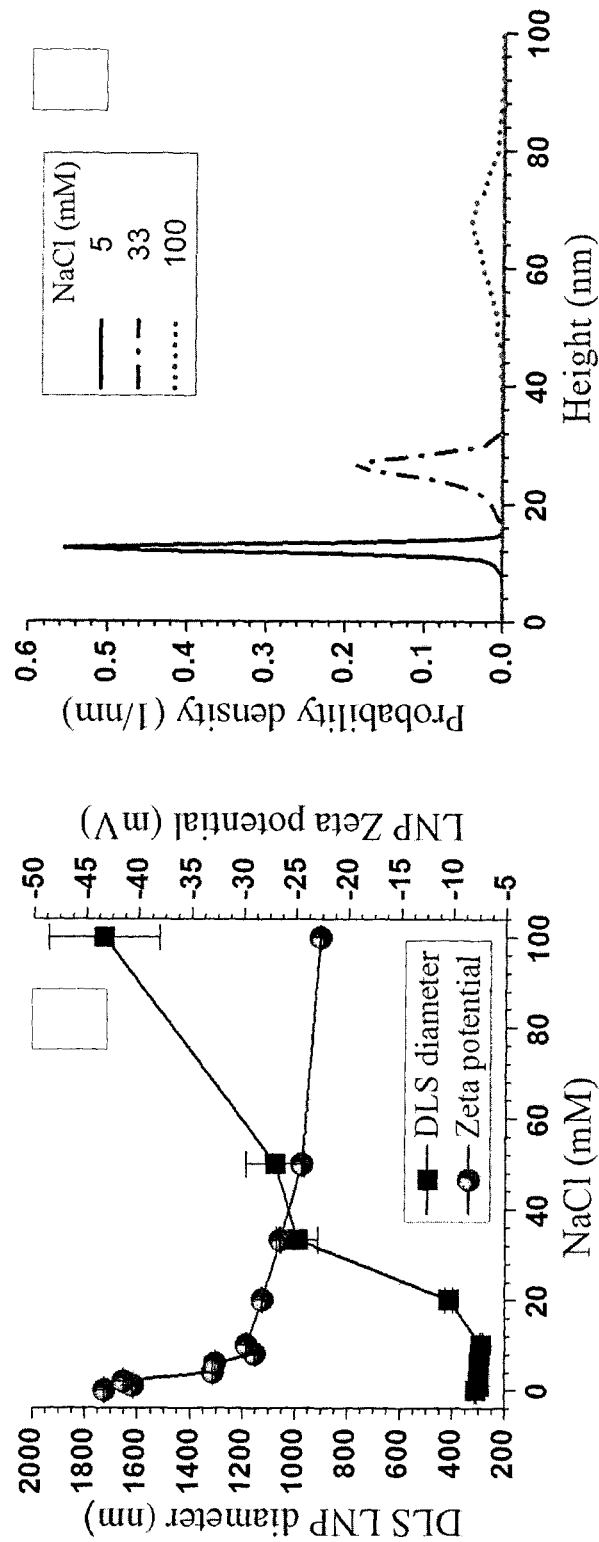
FIG. 23A is a graph of LNP particle size and zeta potential for the LNPs of Example 12 as a function of NaCl concentration.
FIG. 23B is a graph of AFM height measurements for the LNPs of FIG. 23A at different NaCl concentrations.

The result of the dilution experiments showed that ionic strength affected colloidal suspension precipitation behavior by affecting the double electric layer surrounding the LNP surface. The effect of ionic strength on LNP size was evaluated by spiking a NaCl solution into a dialyzed LNP suspension of pH 6.4. As the concentration of NaCl was increased to 20 mM, the zeta-potential of the LNP was decreased (in absolute value) from approximately −50 mV to −25 mV, at which point there was a rapid increase in particle size due to aggregation, as shown in FIG. 23A. This critical zeta-potential of −25 mV is in agreement with that observed in the pH effect study (FIG. 21A). The aggregation phenomenon is clearly shown by AFM imaging, as shown in FIGS. 24A, 24B, and 24C as well as AFM measured height distributions (FIG. 23B).

Figure 25:
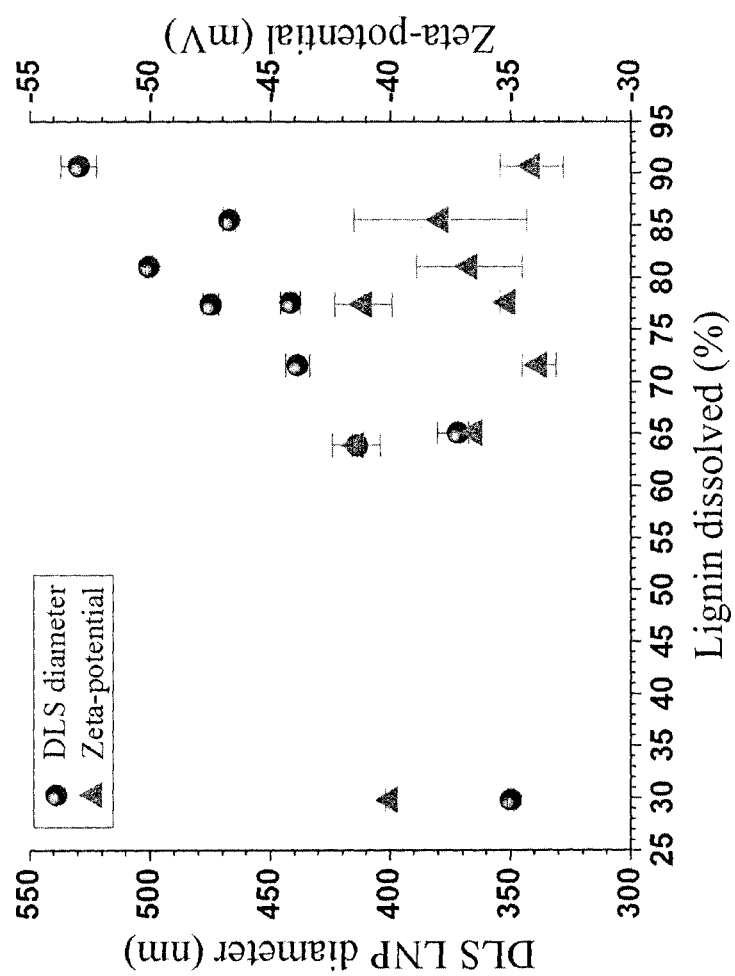
FIG. 25 is a graph of LNP particle size and zeta potential for the LNPs of Example 12 as a function of dissolved lignin content.

Fractionation conditions also affected the LNP size. As listed in Table 7, more severe reaction conditions resulted in a larger LNP particle size for both NE222 and Douglas-fir. In addition, more severe reaction conditions often resulted in increased dissolution of lignin. The amount of lignin dissolved and DLS measured LNP size were correlated as shown in FIG. 25 (NE222). More lignin dissolution resulted in a higher LNP concentration in the diluted spent liquor at 10 wt %. A higher lignin concentration certainly could have increased aggregation, simply due to the increased collision probability among lignin particles. The amount of lignin dissolved in a spent liquor was determined from the lignin mass balance by evaluating the residual lignin in the washed water insoluble solids. As a verification, the amount of dissolved lignin was also determined by diluting the spent liquor to 4% to fully precipitate dissolved lignin. The precipitated lignin was then washed thoroughly. The oven dry weight of the washed lignin was measured gravimetrically for yield determination (listed in Table 7). Discrepancies existed between these two methods (Table 7), perhaps due to losses in precipitation and washing.

TABLE 7

Lignin nanoparticles from different treatment of poplar and Douglas fir measured from the spent acid solution diluted to 10%.

| Biomass Species | Treatment Condition | Lignin dissolved (%) Solid | Lignin dissolved (%) Liquor | Diameter nm | Zeta Potential mV |
|---|---|---|---|---|---|
| NE222 | P70T50t20 | 29.8 | 25.0 | 349.7 ± 1.5 | −40.0 ± 0.2 |
|  | P70T65t20 | 65.1 | 63.9 | 371.7 ± 8.4 | −36.5 ± 0.2 |
|  | P70T65t35 | 63.9 | 60.3 | 413.7 ± 2.1 | −41.4 ± 1.0 |
|  | P70T80t20 | 77.6 | 68.2 | 441.5 ± 4.2 | −35.1 ± 0.3 |
|  | P75T65t20 | 71.6 | 63.9 | 438.6 ± 5.1 | −33.8 ± 0.7 |
|  | P75T65t35 | 77.4 | 60.7 | 474.8 ± 3.2 | −41.1 ± 1.2 |
|  | P75T65t60 | 81.0 | 58.7 | 500.4 ± 1.6 | −36.7 ± 2.2 |
|  | P75T80t20 | 85.5 | 73.7 | 467.1 ± 2.5 | −37.9 ± 3.6 |
|  | P80T80t20 | 90.7 | 78.6 | 529.6 ± 7.4 | −34.1 ± 1.3 |
| Fir | P70T80t20 | 26.5 | 25.0 | 518.5 ± 4.6 | −36.7 ± 0.9 |
|  | P75T80t20 | 36.3 | 26.1 | 605.3 ± 17.9 | −35.2 ± 0.7 |
|  | P80T80t20 | 53.9 | 52.6 | 888.4 ± 122.7 | −32.9 ± 0.5 |

Table 7 also indicates that LNPs from softwood have a much larger size than that from poplar NE222. All LNPs from different fractionation conditions have very high negative zeta potential as listed in Table 7, indicating that all LNPs could be well dispersed in liquids.

Example 13: Lignin Nanoparticle Size Stability

Figure 26:
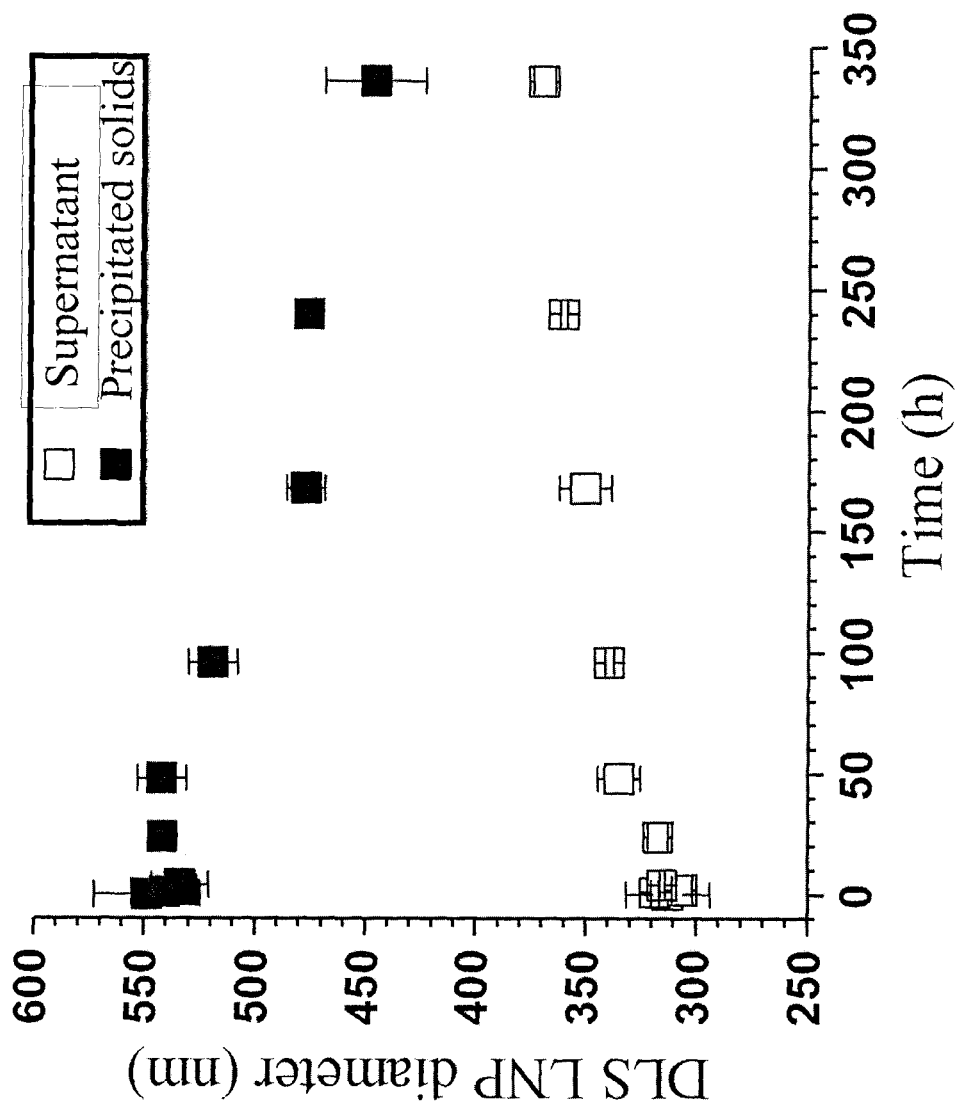
FIG. 26 is a graph of the colloidal stabilities of LNPs in a supernatant from a centrifuge and in a suspension of re-suspended precipitates over a period of two weeks.
Figure 27:
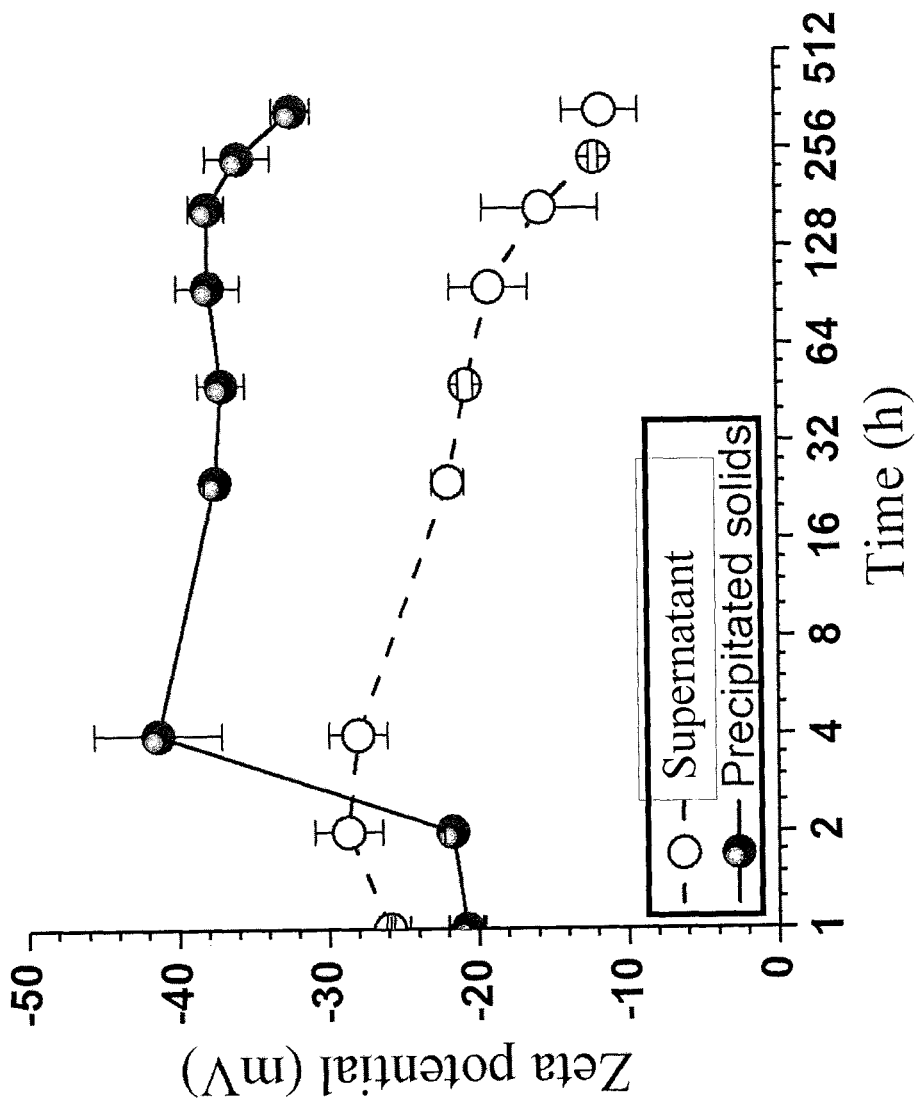
FIG. 27 is a graph of the zeta potential of LNPs in a supernatant from a centrifuge and in a suspension of re-suspended precipitates over a period of two weeks.
Figure 28B:
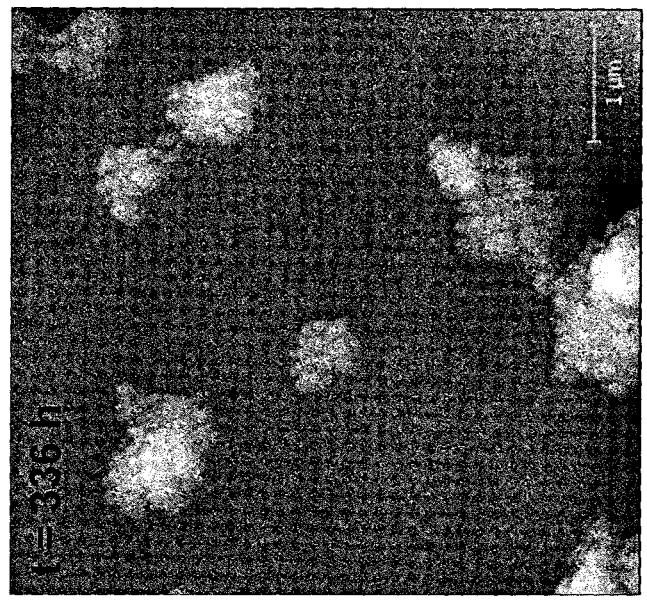
FIG. 28B is an AFM image of the LNPs in a supernatant at t=336 hours, as described in Example 14.
Figure 28A:
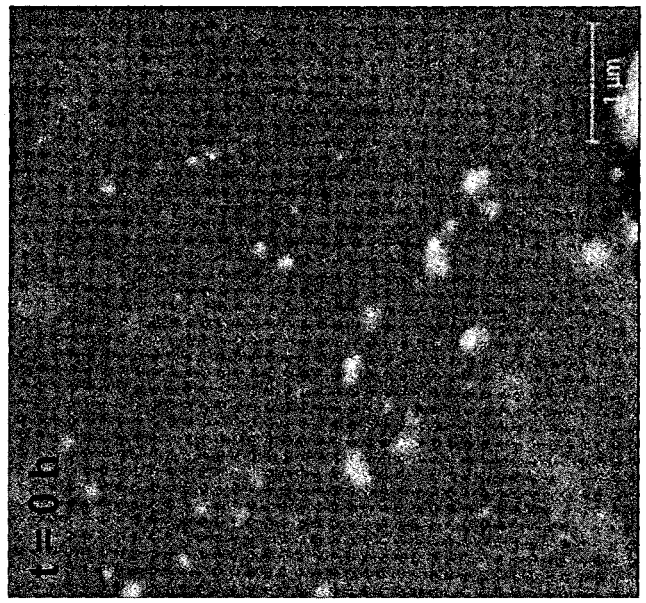
FIG. 28A is an AFM image of the LNPs in a supernatant at t=0 hours.
Figure 29:
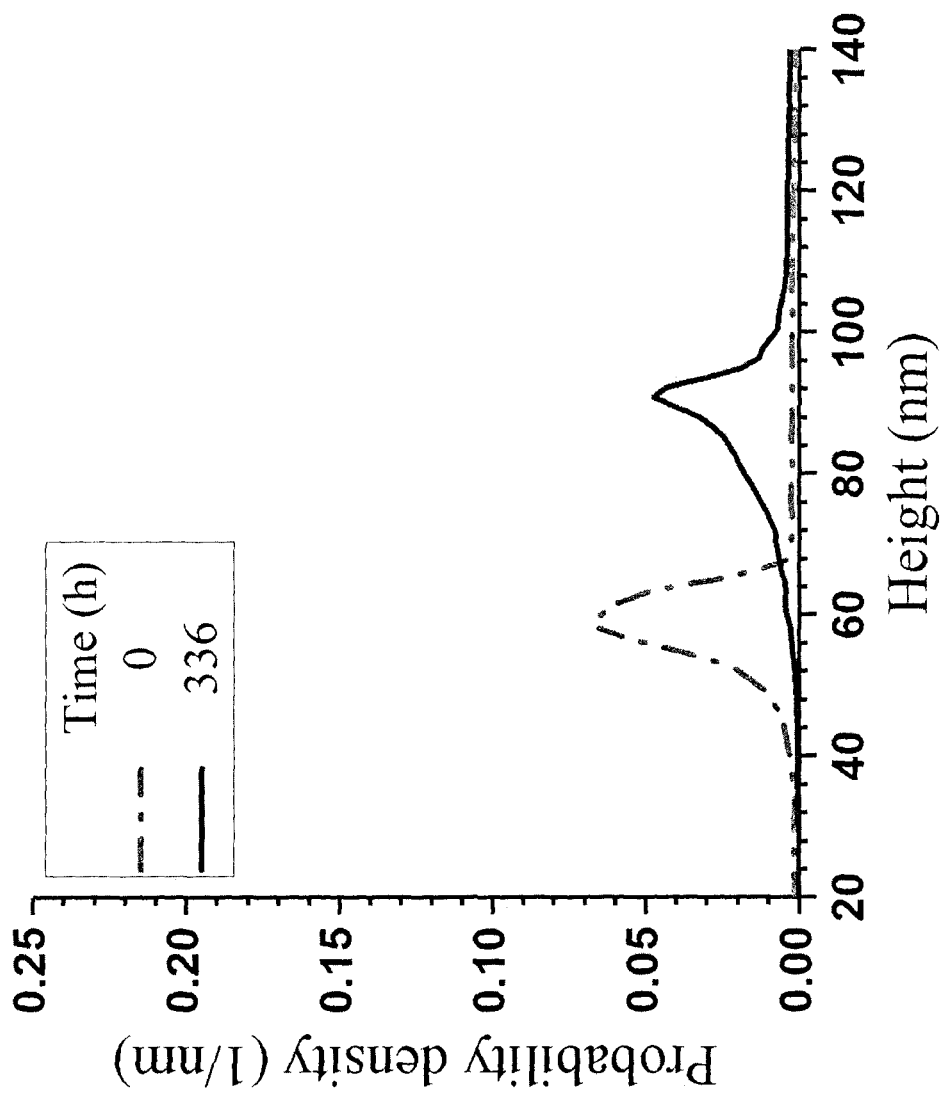
FIG. 29 is a graph of AFM height measurements of the samples of FIGS. 28A and 28B.

Colloidal stability of LNPs is important for a variety of applications. The diluted p-TsOH spent liquor from P75T80t20 at 40 wt % was used to study LNP colloidal stability. The spent liquor was further diluted to 10 wt %, then dialyzed to a pH of approximately 4.5. The dialyzed LNP suspension was then centrifuged at 3000 g for 10 min. The precipitated lignin from centrifugation was re-suspended in DI water. The stabilities of the LNPs in the supernatant from the centrifuge and in the suspension of re-suspended precipitates were analyzed periodically using dynamic light scattering (DLS) for a period of two weeks. Samples of each suspension was first vigorously hand shaken each time before DLS analyses. AFM images of each suspension at time zero and at the end of two weeks were also taken. DLS analyses show that the DLS size of the LNPs in the supernatant was slightly increased gradually during a period of two weeks from approximately 310 nm to 370 nm (FIG. 26). Over the same period, mean zeta-potential gradually decreased from −28 mV to −11 mV (FIG. 27). AFM images obtained at time 0 and after two weeks confirmed the increase in LNP size (FIGS. 28A and 28B). The increase in LNP size was a direct result of particle aggregation. This aggregation also increased the particle thickness as shown by the AFM measured particle height probability density (FIG. 29).

Figure 30A:
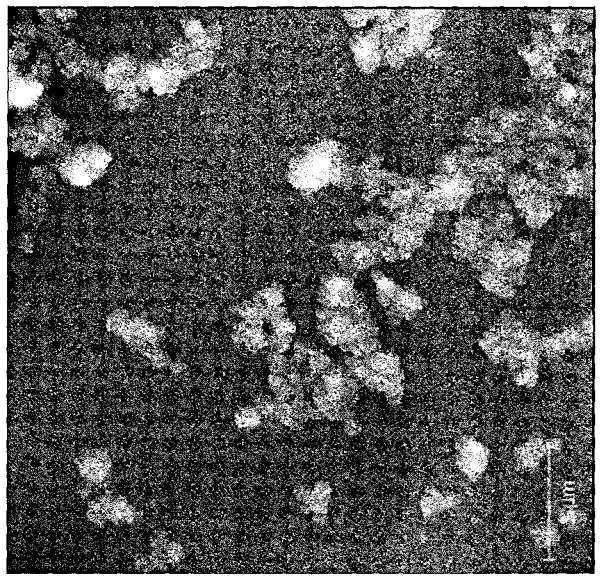
FIG. 30A is an AFM image of LNPs from a suspension of re-suspended precipitates.
Figure 30B:
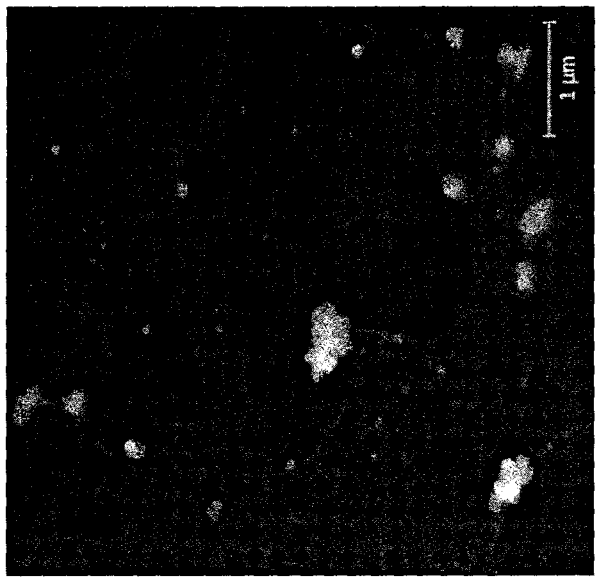
FIG. 30B is an AFM image of LNPs from a suspension of re-suspended precipitates from a centrifuge at t=0.
Figure 31:
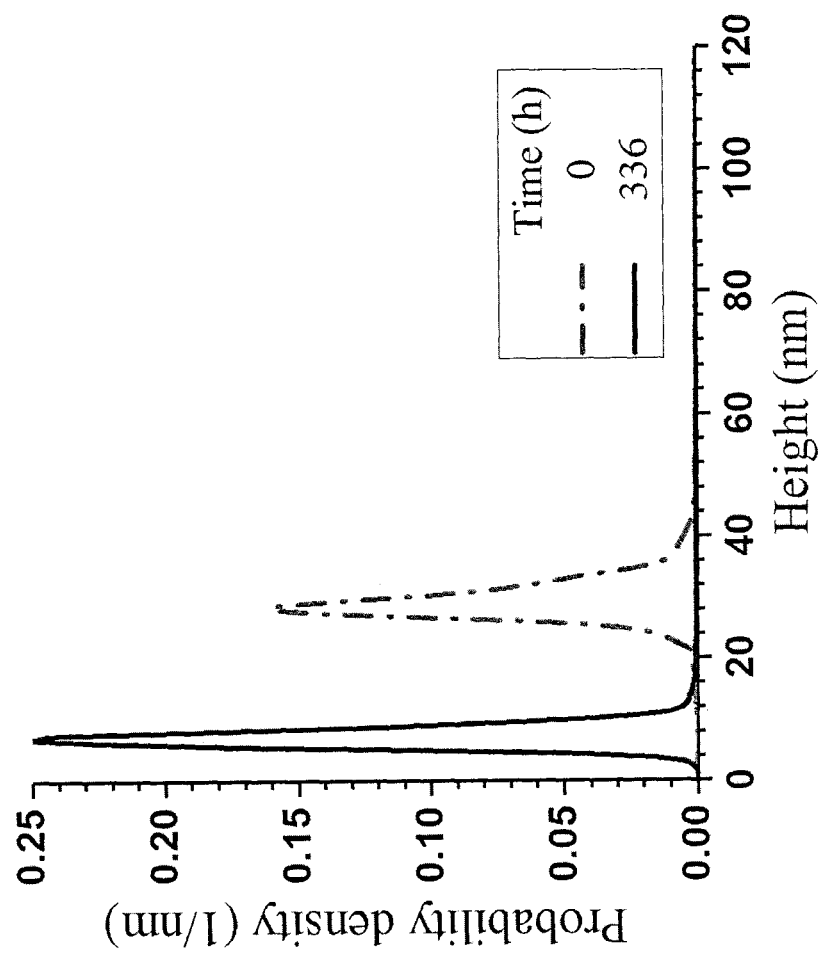
FIG. 31 is a graph of AFM height measurements of the LNPs in FIG. 30A at t=0 and in FIG. 30B at t=336 hours.

DLS-measured mean size of LNPs in the suspension of the re-suspended precipitated lignin decreased over a period of two weeks from 540 nm to 450 nm (FIG. 26). The resuspension of these precipitated particles in DI water increased the pH of the suspension, which resulted in a high surface charge (FIG. 27), according to the results shown in FIGS. 21A and 21B, and prevented aggregation during drying for AFM imaging. The AFM-measured particle thickness measurements (FIG. 31) were qualitatively in agreement with the DLS size measurements. FIG. 30A is an AFM image of LNPs from a suspension of re-suspended precipitates. FIG. 30B is an AFM image of LNPs in a supernatant from a centrifuge at t=0.

Example 14: p-TsOH-Based Delignification for Wood Fiber Production Using Birch Wood The birch MDF described in Example 6 was used to produce corrugated medium fibers through p-TsOH-based lignocellulosic biomass fractionation. Most of the data listed in Table 8 were obtained from Example 6, but are presented in terms of component yields in theoretical percentages as compared to mass-based component yields in Table 6. Different degrees of delignification could be achieved by varying reaction severity. The scale-up run T50P81t27, using 750 g in oven dry (OD) weight MDF, resulted in similar results as the lab scale run T50P80t20. The scale-up run had slightly increased delignification due to a slightly longer reaction time of 27 min (including a 0.5*heat-up period of 14 min).

TABLE 8

Chemical compositions of p-TsOH fractionated birch MDF samples under different conditions. The numbers in the parentheses are component recovery yields theoretical percentages.

| Sample Label[1] | Solids yield (%) | Glucan (%) | Xylan (%) | Mannan (%) | Lignin (%) |
|---|---|---|---|---|---|
| Untreated Birch |  | 36.2 | 22.5 | 1.2 | 22.5 |
| Birch MDF | 100.0 | 34.6 | 20.8 | 1.9 | 23.0 |
| P40T80t55 | 60.6 | 51.7 (90.5) | 13.3 (38.8) | 2.3 (73.7) | 17.6 (46.4) |
| P50T80t20 | 56.7 | 59.2 (97.0) | 15.0 (40.8) | 2.4 (70.8) | 16.0 (39.3) |
| P50T80t40 | 59.6 | 53.7 (92.4) | 13.0 (37.3) | 2.0 (63.5) | 15.3 (39.5) |
| P50T80t80 | 56.5 | 61.1 (99.8) | 11.9 (30.9) | 2.4 (72.5) | 13.8 (34.0) |

TABLE 8-continued

Chemical compositions of p-TsOH fractionated birch MDF samples under different conditions. The numbers in the parentheses are component recovery yields theoretical percentages.

| Sample Label[1] | Solids yield (%) | Glucan (%) | Xylan (%) | Mannan (%) | Lignin (%) |
|---|---|---|---|---|---|
| P65T80t20 | 54.2 | 62.0 (97.0) | 14.0 (36.4) | 2.6 (74.9) | 11.6 (27.4) |
| P80T80t20 | 51.3 | 67.7 (100.4) | 12.2 (30.0) | 2.5 (68.2) | 7.2 (16.0) |
| P50T81t27[2] | 52.8 | 57.7 (89.8) | 14.7 (36.7) | 2.7 (74.6) | 15.1 (35.4) |

[1](Pxx, Txx, txx) stands for p-TsOH concentration in wt %, reaction temperature in °C. and reaction duration in min.
[2]scale-up run at 750 g, average temperature.

Figure 32A:
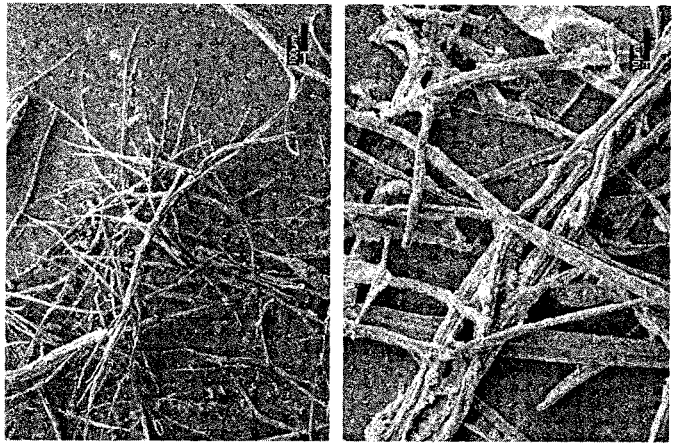
FIG. 32A shows an optical micrograph image (left panel) and a scanning electron microscope (SEM) image (right panel) of MDF fibers before delignification.
Figure 32B:
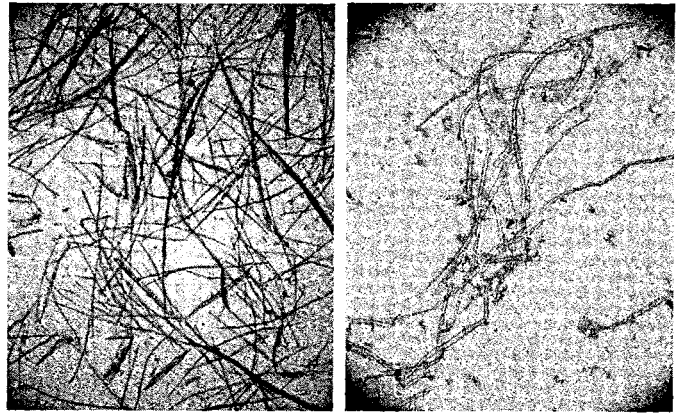
FIG. 32B shows an optical micrograph (left panel) and an SEM image (right panel) of MDF fibers after delignification.

Based on the amount of lignin removal from the lab bench scale run, a targeted reaction condition of P50T80t20 was chosen for a scale-up study to produce corrugated medium fibers. The actual reaction condition P50T81t27 deviated slightly due to difficulties in controlling the exact temperature using steam-jacket heating and the increased heat-up period of the larger scale-up reactor. The lignin content of the p-TsOH-based fractionation of the fibers was 15% (Table 8) after solubilizing 65% of the wood lignin. This lignin content is about the same as that of typical corrugated medium pulp fibers. The morphologies of the delignified fibers are shown in FIG. 32B in comparison with the initial MDF fibers in FIG. 32A. Typical MDF fibers have a length over 2 mm, due mainly to the presence of many fiber bundles. The p-TsOH treatment separated the fiber bundles. The length of these separated fibers was over 1 mm. Refining reduced fiber length, but improved fiber fibrillation, as can be seen from the optical and scanning electronic microscopic (SEM) images (FIGS. 33A and 33B).

Figures 34A, 34B:
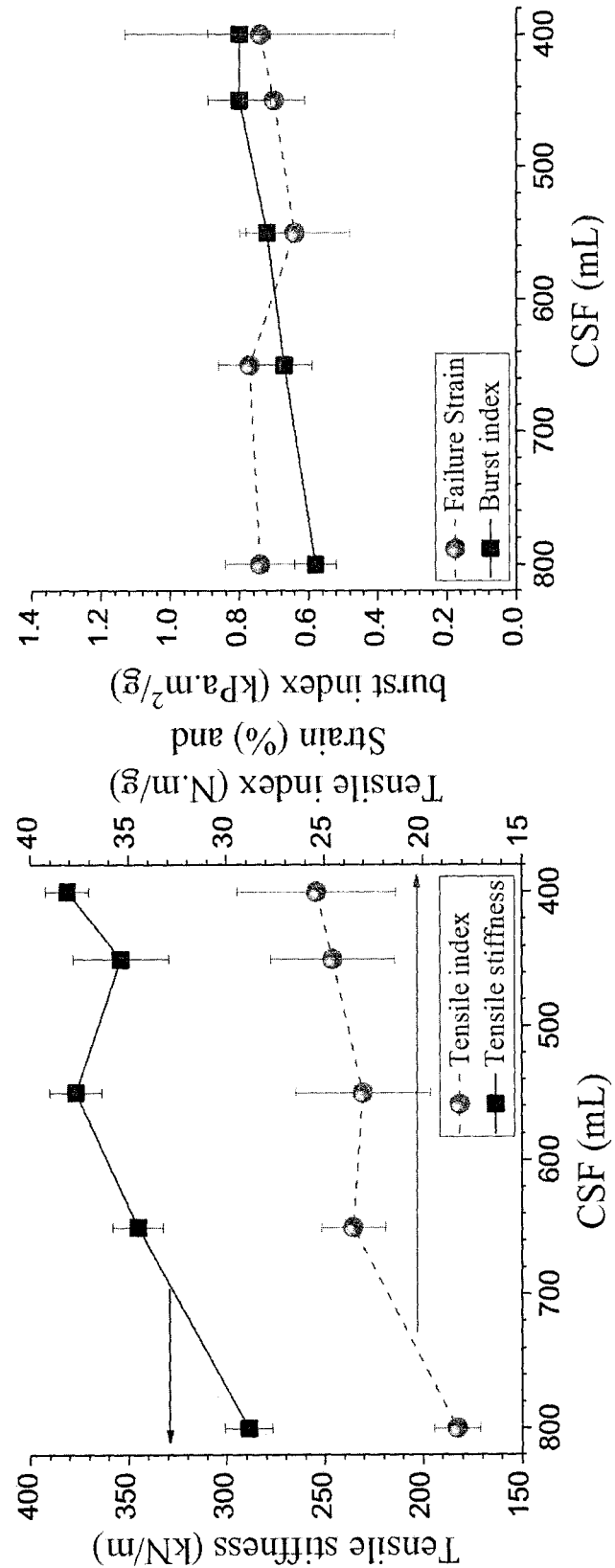
FIG. 34A is a graph of the tensile index as a function of CSF for a birch MDF sheet.
FIG. 34B is a graph of the failure strain as a function of CSF for a birch MDF sheet.

Due to difficulties in making high basis weight sheets in the laboratory, the initial studies on the mechanical properties are from sheets with basis weight of 60 g·m$^{-2}$. The results indicate that a tensile index of approximately 25 N·m·g$^{-1}$ was achieved after refining to approximately 500 (mL) Canadian Standard Freeness (CSF) (FIG. 34A). The failure strain is shown in FIG. 34B.

Example 15: p-TsOH-Based Fractionation of an Agricultural Residue: Wheat Straw

Lightly hammer-milled wheat straw was fractionated directly using concentrated p-TsOH solution in a range of conditions similar to that described in Example 1. The wheat straw was first water washed to remove dirt. Good selectivity in dissolving lignin over cellulose was obtained, as listed in Table 9. At a relatively low p-TsOH acid concentration of 40 w %, over 50% straw lignin dissolved while over 85% of cellulose was retained. Wheat straw usually contains a substantial amount of silicate, as can be seen from the high ash content of 5.1% listed in Table 9 (obtained by burning at 560° C. the residual solids after a two-step sulfuric acid hydrolysis of carbohydrates). It appears that silicate was fully retained in the WIS after p-TsOH-based lignocellulosic biomass fractionation. This is beneficial, as it helps to increase the WIS yield for material production as well as avoiding silicate-caused equipment corrosion problems in downstream processing. The silicate can also improve the hydrophobicity of the solids for LCNF or LCMF production.

TABLE 9

Chemical compositions of p-TsOH-based fractionation of wheat straw samples under different conditions. The numbers in the parentheses are component yields based on the component in the untreated wheat straw.

| Sample Label[1] | Solids yield (%) | Glucan (%) | Xylan (%) | Ash (%) | K. Lignin (%) |
|---|---|---|---|---|---|
| Untreated Wheat Straw | 100 | 40.8 | 24.5 | 5.1 | 20.4 |
| P20T40t20 | 94.7 | 41.4 (95.9) | 22.9 (88.3) | 5.3 (97.7) | 20.7 (96.2) |
| P20T50t20 | 93.3 | 39.5 (90.2) | 21.8 (82.8) | 5.5 (100.4) | 19.9 (91.2) |
| P20T60t20 | 89.8 | 38.3 (84.2) | 21.5 (78.5) | 6.4 (111.9) | 19.5 (85.9) |
| P25T60t30 | 87.3 | 41.1 (88.0) | 22.0 (78.3) | 5.2 (87.7) | 19.0 (81.7) |
| P25T60t30R | 87.3 | 41.7 (89.2) | 22.9 (81.4) | 6.1 (103.6) | 19.8 (85.1) |
| P35T60t30 | 80.5 | 43.2 (85.2) | 20.5 (67.4) | 8.2 (128.1) | 20.7 (81.8) |
| P35T60t60 | 75.5 | 45.4 (84.0) | 17.9 (55.2) | 7.1 (104.2) | 19.1 (70.7) |
| P40T70t60 | 67.1 | 48.3 (79.4) | 14.9 (40.7) | 9.0 (117.4) | 17.8 (58.5) |
| P40T80t60 | 66.0 | 54.7 (88.6) | 13.4 (36.1) | 8.9 (114.1) | 16.9 (54.8) |
| P40T80t60R | 66.0 | 52.5 (84.9) | 13.3 (35.9) | 7.6 (97.2) | 17.2 (55.8) |
| P40T80t90 | 58.3 | 57.7 (80.4) | 12.0 (27.9) | 9.2 (104.0) | 16.3 (46.8) |
| P40T80t120 | 62.3 | 56.3 (88.1) | 11.7 (30.5) | 9.2 (111.8) | 15.8 (48.4) |
| P50T80t60 | 57.2 | 55.1 (77.1) | 11.4 (26.5) | 9.5 (105.5) | 14.4 (40.5) |
| P50T80t90 | 56.0 | 59.0 (80.9) | 10.9 (24.9) | 9.2 (99.8) | 14.0 (38.6) |
| P60T80t60 | 55.0 | 62.1 (83.8) | 10.0 (22.4) | 8.5 (91.2) | 11.2 (30.3) |
| P60T80t90 | 55.0 | 59.3 (79.9) | 8.5 (19.1) | 10.1 (108.4) | 14.0 (37.9) |

[1] (Pxx, Txx, txx) stands for p-TsOH concentration in wt %, reaction temperature in °C. and reaction duration in min. R stands for replicate fractionation run. R stands for replicate fractionation run.

Example 16: p-TsOH-Based Fractionation of an Energy Crop: Switchgrass

Mildly hammer-milled switchgrass was also fractionated using concentrated p-TsOH solution in the range of conditions used for the wheat straw in Example 14. The switchgrass was also washed and air dried before use. Again, good selectivity of dissolved lignin over cellulose was achieved. The relatively lower dissolution of lignin of approximately 60% compared to 85% for wood described previously was perhaps due to the relatively larger size of the materials as well as the relatively low p-TsOH concentrations used in the p-TsOH-based fractionation. Further hammer-milling the switchgrass is expected to achieve improved dissolution of lignin.

TABLE 10

Chemical compositions of p-TsOH-based fractionation of switchgrass samples under different conditions. The numbers in the parentheses are component yields based on the component in the untreated switchgrass.

| Sample Label [1] | Solids yield (%) | Glucan (%) | Xylan (%) | K. Lignin (%) |
|---|---|---|---|---|
| Untreated Switchgrass | 100 | 37.3 | 26.1 | 23.5 |
| P20T40t20 | 91.4 | 40.1 (98.2) | 25.2 (88.5) | 23.0 (89.5) |
| P20T50t20 | 90.2 | 39.6 (95.7) | 26.5 (91.6) | 23.7 (91.0) |
| P20T60t20 | 89.6 | 40.3 (96.9) | 25.5 (87.6) | 24.4 (93.2) |
| P25T60t30 | 87.8 | 39.4 (92.7) | 26.4 (88.9) | 24.2 (90.5) |
| P25T60t30R | 87.8 | 40.7 (95.8) | 25.6 (86.2) | 23.1 (86.4) |
| P35T60t30 | 83.4 | 41.7 (93.2) | 25.4 (81.1) | 24.8 (87.9) |
| P35T60t60 | 76.4 | 42.3 (86.6) | 20.7 (60.7) | 24.9 (81.2) |
| P40T70t60 | 68.2 | 51.7 (94.5) | 19.8 (51.8) | 23.9 (69.4) |
| P40T80t60 | 59.7 | 52.5 (83.9) | 14.5 (33.2) | 22.7 (57.6) |
| P40T80t90 | 59.4 | 48.8 (94.4) | 13.2 (30.0) | 21.3 (53.9) |
| P40T80t120 | 59.3 | 59.2 (78.6) | 12.5 (28.4) | 19.9 (50.3) |
| P50T80t60 | 57.4 | 49.4 (88.5) | 13.5 (29.8) | 20.7 (50.5) |
| P50T80t90 | 55.1 | 57.5 (86.9) | 13.5 (28.4) | 19.0 (44.6) |
| P60T80t60 | 55.1 | 58.9 (93.2) | 12.0 (25.4) | 19.6 (45.9) |
| P60T80t90 | 52.9 | 63.1 (92.3) | 11.1 (22.5) | 18.7 (42.1) |

[1] (Pxx, Txx, txx) stands for p-TsOH concentration in wt %, reaction temperature in °C. and reaction duration in min. R stands for replicate fractionation run. R stands for replication fractionation runs.

Figures 35A, 35B:
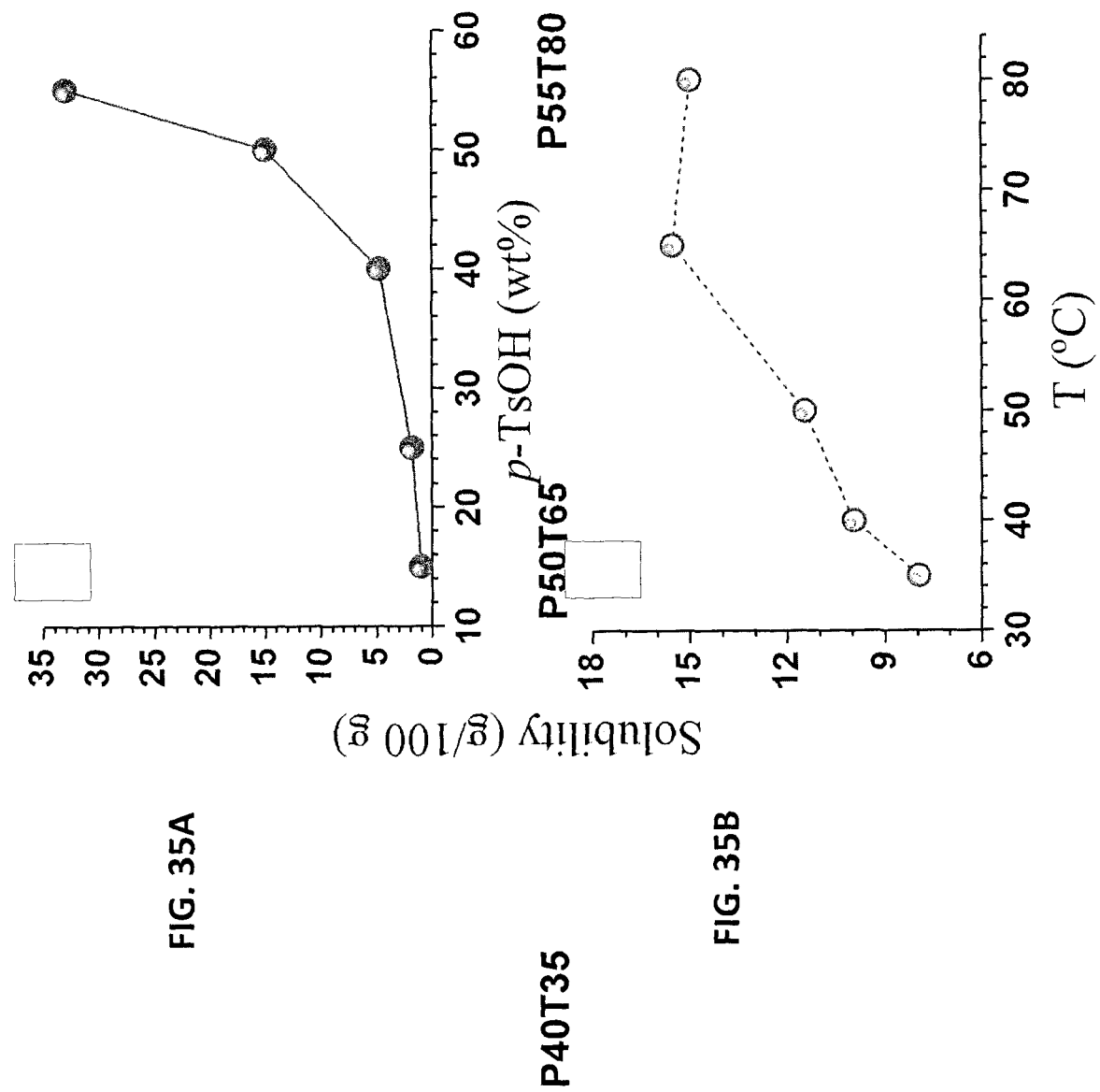
FIG. 35A is a graph of the solubility of alkali technical lignin as a function of p-TsOH concentration.
FIG. 35B is a graph of the solubility of alkali technical lignin as a function of solution temperature.
Figure 36C:
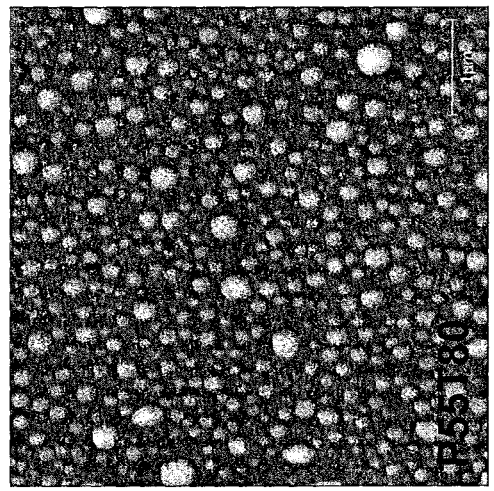
FIG. 36C is an AFM image of precipitated LNPs from sample P55T80.
Figure 36B:
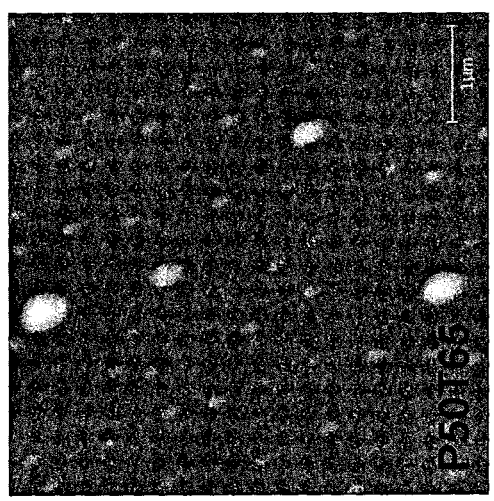
FIG. 36B is an AFM image of precipitated LNPs from sample P50T65.
Figure 36A:
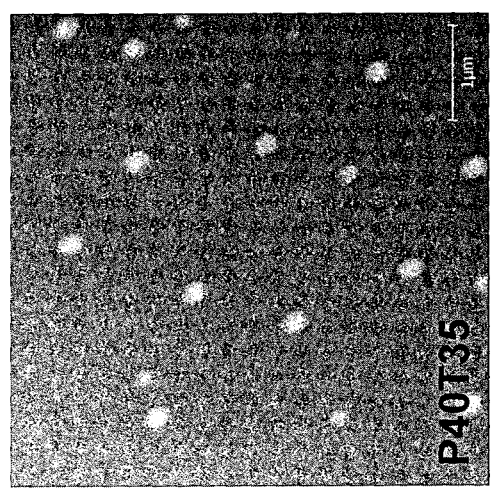
FIG. 36A is an AFM image of precipitated LNPs from sample P40T35.
Figure 37:
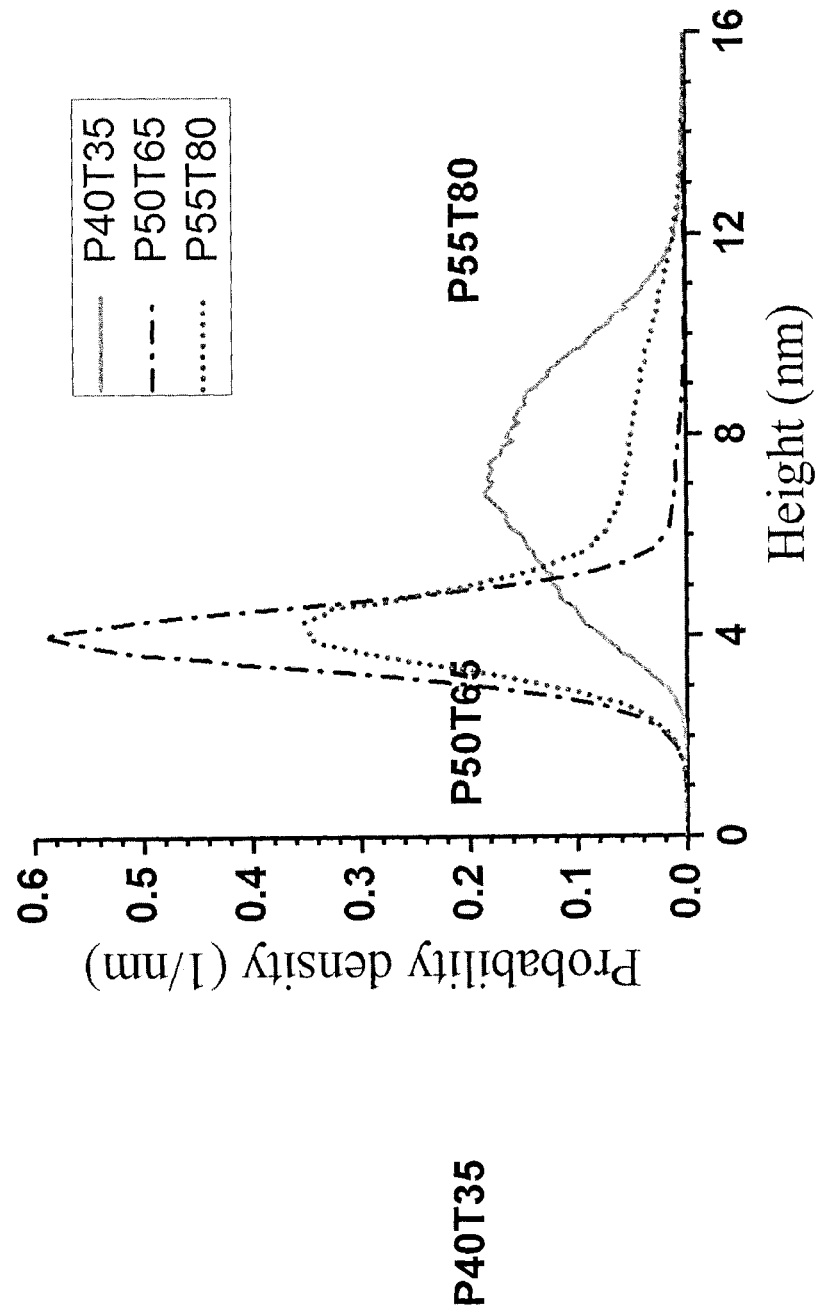
FIG. 37 is a graph of AFM height measurements of the samples of FIGS. 36A-36C.

Example 17: Solubilization of Commercial Technical Lignin Using an Aqueous p-TsOH Solution Commercial lignin is readily available but cannot be solubilized in aqueous systems to produce micro or nanoparticles. Aqueous p-TsOH was also used to solubilize commercial alkali technical lignin purchased from Sigma-Aldrich (St. Louis, Mo.). At a given temperature of 80° C., alkali lignin was gradually added into a 100 g of p-TsOH solution with stirring until the solution could no longer solubilize lignin, as observed from precipitation. The solubility was the maximal amount of lignin solubilized in the 100 g solution. As shown in FIG. 35A, lignin solubility at 80° C. was increased with p-TsOH concentration. Solubility increased rapidly at p-TsOH concentrations above 40 wt %, with a solubility of 35 g/100 g at a p-TsOH concentration of 55 wt %. Lignin solubility was also increased with temperature, as shown in FIG. 35B, and reached a plateau at approximately 65° C. at a p-TsOH concentration of 50 wt %. The solubilized lignin was separated through centrifugation after diluting the solution to 10 wt % with water to precipitate lignin. AFM images revealed that the precipitated LNPs had a circular shape with a lateral diameter of approximately 100-200 nm, as shown in FIGS. 36A, 36B, and 36C. The AFM topographic measured heights indicated average heights were approximately 4-6 nm, as shown in FIG. 37. Gel permeation chromatography (GPC) molecular measurements indicated that Mw was approximately 7000, as listed in Table 11, except for the run at a severe condition of P55T80.

TABLE 11

GPC measured molecular weight of LNPs from solubilizing alkali lignin in p-TsOH solutions

| Run | Mn | Mw | PDI |
|---|---|---|---|
| P40T35 | 1791 | 7480 | 4.18 |
| P40T65 | 1812 | 7098 | 3.91 |
| P50T65 | 1774 | 7282 | 4.10 |
| P55T80 | 2130 | 11934 | 5.60 |

REFERENCES

Ago M, Huan S, Borghei M, Raula J, Kauppinen E I, Rojas O J. 2016. High-throughput synthesis of lignin particles (~30 nm to ~2 μm) via aerosol flow reactor: Size fractionation and utilization in pickering emulsions. ACS Applied Materials and Interfaces 8(35):23302-23310.

Balasubramanian D, Srinivas V, Gaikar V G, Sharma M M. 1989. Aggregation Behavior of Hydrotropic Compounds in Aqueous-Solution. Journal of Physical Chemistry 93(9):3865-3870.

Davis M W. 1998. A rapid modified method for compositional carbohydrate analysis of lignocellulosics by high pH anion-exchange chromatography with pulsed amperometric detection (HPAEC/PAD). Journal of Wood Chemistry and Technology 18(2):235-352.

Duval A, Lawoko M. 2014. A review on lignin-based polymeric, micro- and nano-structured materials. Reactive & Functional Polymers 85:78-96.

Frangville C, Rutkevicius M, Richter A P, Velev O D, Stoyanov S D, Paunov V N. 2012. Fabrication of Environmentally Biodegradable Lignin Nanoparticles. Chemphyschem 13(18):4235-4243.

Gabov K, Fardim P, da Silva Junior G. 2013. Hydrotropic fractionation of birch wood into cellulose and lignin: A new step towards green biorefinery. BioResources 8(3): 3518-3530.

Gabov K, Gosselink R J A, Smeds A I, Fardim P. 2014. Characterization of lignin extracted from birch wood by a modified hydrotropic process. Journal of Agricultural and Food Chemistry 62(44):10759-10767.

Gromov V S, Odincov P N. 1959. Certain characteristics and ways of improving the hydrotropic method to obtain pulp. Tr. Inst. Lesokhoz. Probl. i Khim. Drev. Akad. Nauk Latv. SSR 17:93-103.

Hatzopoulos M H, Eastoe J, Dowding P J, Rogers S E, Heenan R, Dyer R. 2011. Are Hydrotropes Distinct from Surfactants? Langmuir 27(20):12346-12353.

Hauru L K J, Ma Y, Hummel M, Alekhina M, King A W T, Kilpelainen 1, Penttila P A, Serimaa R, Sixta H. 2013. Enhancement of ionic liquid-aided fractionation of birchwood. Part 1: autohydrolysis pretreatment. RSC Adv. 3:16365-16373.

Jiang C, He H, Jiang H, Ma L, Jia D M. 2013. Nano-lignin filled natural rubber composites: Preparation and characterization. Express Polymer Letters 7(5):480-493.

Kalninsh A I, Odincov P N, Gromov V S. 1967. Birchwood delignification. Cellul. Chem. Technol. 1 (4):461-469.

Kalninsh A I, Surna J A, Zoldners J A. 1962. The utilization of hydrotropic lignin for the preparation of molding powders. Tr. Inst. Lesokhoz. Probl. i Khim. Drev. Akad. Nauk Latv. SSR 24:65-70.

Kamaly N, Yameen B, Wu J, Farokhzad O C. 2016. Degradable Controlled-Release Polymers and Polymeric Nanoparticles: Mechanisms of Controlling Drug Release. Chemical Reviews 116(4):2602-2663.

Korpinen R, Fardim P. 2009. Lignin extraction from wood biomass by a hydrotropic solution. O Papel (Brazil) 70(5):69-82.

Lievonen M, Valle-Delgado J J, Mattinen M L, Hult E L, Lintinen K, Kostiainen M A, Paananen A, Szilvay G R, Setala H, Osterberg M. 2016. A simple process for lignin nanoparticle preparation. Green Chemistry 18(5):1416-1422.

Luo X, Gleisner R, Tian S, Negron J, Horn E, Pan X J, Zhu J Y. 2010. Evaluation of mountain beetle infested lodgepole pine for cellulosic ethanol production by SPORL pretreatment. Ind. Eng. Chem. Res. 49(17):8258-8266.

Mavila S, Eivgi O, Berkovich I, Lemcoff N G. 2016. Intramolecular Cross-Linking Methodologies for the Synthesis of Polymer Nanoparticles. Chemical Reviews 116 (3):878-961.

McKee R H. 1943. Recovery of cellulose and lignin from wood. U.S. Pat. No. 2,308,564.

McKee R H. 1946. Use of hydrotropic solutions in industry. Ind. Eng. Chem. 38(4):382-384.

McKee R H. 1954. Comparison of wood pulping processes. Pulp Pap. Mag. Can 55(2):64-66.

Moon R J, Martini A, Nairn J, Simonsen J, Youngblood J. 2011. Cellulose nanomaterials review: structure, properties and nanocomposites. Chem. Soc. Rev. 40:3941-3994.

Nair S S, Sharma S, Pu Y Q, Sun Q N, Pan S B, Zhu J Y, Deng Y L, Ragauskas A J. 2014. High Shear Homogenization of Lignin to Nanolignin and Thermal Stability of Nanolignin-Polyvinyl Alcohol Blends. Chemsuschem 7(12):3513-3520.

Nelson K, Retsina T, Pylkkanen V, O'Connor R. 2015. Processes and apparatus for producing nanocellulose, and compositions and products produced therefrom. U.S. Pat. No. 9,187,865 B2.

Nelson P J. 1978. Hydrotropic pulping of E. Regnans wood. APPITA 31 (6):437-442.

Procter A R. 1971. A review of hydrotropic pulping. Pulp Pap. Mag. Can. 72(8):67-74.

Qian Y, Zhang Q, Qiu X Q, Zhu S P. 2014. CO2-responsive diethylaminoethyl-modified lignin nanoparticles and their application as surfactants for CO2/N-2-switchable Pickering emulsions. Green Chemistry 16(12):4963-4968.

Reisch A, Klymchenko A S. 2016. Fluorescent Polymer Nanoparticles Based on Dyes: Seeking Brighter Tools for Bioimaging. Small 12(15):1968-1992.

Richter A P, Bharti B, Armstrong H B, Brown J S, Plemmons D, Paunov V N, Stoyanov S D, Velev O D. 2016. Synthesis and characterization of biodegradable lignin nanoparticles with tunable surface properties. Langmuir 32(25):6468-6477.

Richter A P, Brown J S, Bharti B, Wang A, Gangwal S, Houck K, Cohen Hubal E A, Paunov V N, Stoyanov S D, Velev O D. 2015. An environmentally benign antimicrobial nanoparticle based on a silver-infused lignin core. Nat Nanotechnol 10(9):817-23.

Robert T A. 1955. Hydrotropic pulping of a tropical wood. TAPPI 38(9):149A-150A.

Rojo E, Peresin M S, Sampson W W, Hoeger I C, Vartiainen J, Laine J, Rojas O J. 2015. Comprehensive elucidation of the effect of residual lignin on the physical, barrier, mechanical, and surface properties of nanocellulose films. Green Chem. 17:1853-1866.

Spence K L, Venditti R A, Habibi Y, Rojas O J, Pawlak J J. 2010. The effect of chemical composition on microfibrillar cellulose films from wood pulps: Mechanical processing and physical properties. Bioresource Technology 101 (15):5961-5968.

Ten E, Ling C, Wang Y, Srivastava A, Dempere L A, Vermerris W. 2014. Lignin Nanotubes As Vehicles for Gene Delivery into Human Cells. Biomacromolecules 15(1):327-338.

Upton B M, Kasko A M. 2016. Strategies for the Conversion of Lignin to High-Value Polymeric Materials: Review and Perspective. Chemical Reviews 116(4):2275-2306.

Xia Y, Xiong Y, Lim B, Skrabalak S E. 2009. Shape-controlled synthesis of metal nanocrystals: Simple chemistry meets complex physics? Angewandte Chemie—International Edition 48(1):60-103.

Zhu H, Luo W, Ciesielski P N, Fang Z, Zhu J Y, Henriksson G, Himmel M E, Hu L. 2016. Wood-derived materials for green electronics, biological devices, and energy applications. Chem. Rev. 116(16):9305-9374.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for treating lignocellulosic biomass, the method comprising:
    dispersing a lignocellulosic biomass in an aqueous solution comprising a hydrotropic solid organic acid, wherein the concentration of the hydrotropic solid organic acid in the solution is higher than its minimal hydrotrope concentration;
    maintaining the solution at a temperature and for a time sufficient to dissolve at least 10 wt. % of the lignin in the lignocellulosic biomass; and
    separating the solution and the dispersed lignocellulosic biomass into a spent acid solution comprising dissolved lignin and a water-insoluble cellulose-rich solids fraction comprising water-insoluble lignocellulosic solid residues.

2. The method of claim 1, wherein the temperature is no greater than 100° C. and the time is no greater than 300 minutes.

3. The method of claim 1, wherein the lignocellulosic biomass comprises wood chips, milled wood, commercial technical lignin, or a combination thereof.

4. The method of claim 1, wherein the lignocellulosic biomass is a hardwood and at least 10 wt. % of the lignin in the hardwood is dissolved.

5. The method of claim 1, wherein the lignocellulosic biomass is softwood and at least 10 wt. % of the lignin in the softwood is dissolved.

6. The method of claim 1, wherein the lignocellulosic biomass is commercial technical lignin and the amount of the technical lignin dissolved is at least 2 g/100 g solution.

7. The method of claim 1, further comprising fibrillating the lignocellulosic biomass prior to dispersing the lignocellulosic biomass in the aqueous solution comprising the hydrotropic solid organic acid.

8. The method of claim 1, further comprising precipitating lignin nanoparticles from the spent acid solution.

9. The method of claim 1, further comprising converting sugars dissolved in the spent acid solution into furans and separating the furans from the spent acid solution.

10. The method of claim 1, further comprising mechanically fibrillating the lignocellulosic solid residues to form lignocellulosic microfibrils, lignocellulosic nanofibrils, or a combination thereof.

11. The method of claim 10, wherein the water-insoluble cellulose-rich solids fraction comprises lignocellulosic solid residues and lignocellulosic nanocrystals.

12. The method of claim 10, further comprising separating the lignocellulosic solid residues from the lignocellulosic nanocrystals.

13. The method of claim 1, further comprising converting the water-insoluble lignocellulosic solid residues into sugars via hydrolysis using enzymes or chemicals.

14. The method of claim 1, further comprising recycling the hydrotropic solid organic acid in the spent acid solution back into the aqueous solution comprising the dispersed lignocellulosic biomass.

* * * * *